United States Patent
Thompson et al.

(10) Patent No.: US 12,370,061 B2
(45) Date of Patent: Jul. 29, 2025

(54) ROBOTIC SURGERY SYSTEM FOR AUGMENTED ARTHROPLASTY PROCEDURES

(71) Applicant: MAKO Surgical Corp., Weston, FL (US)

(72) Inventors: Matthew Thompson, Durham, NC (US); Varun Chandra, Weston, FL (US); Mark Nadzadi, Batavia, OH (US); Christine Perrone, Weston, FL (US); Garrett Joyal, Weston, FL (US)

(73) Assignee: MAKO Surgical Corp., Weston, FL (US)

( * ) Notice: Subject to any disclaimer, the term of this patent is extended or adjusted under 35 U.S.C. 154(b) by 414 days.

(21) Appl. No.: 17/939,519

(22) Filed: Sep. 7, 2022

(65) Prior Publication Data
US 2022/0409396 A1    Dec. 29, 2022

Related U.S. Application Data

(63) Continuation of application No. 17/257,162, filed as application No. PCT/US2020/047220 on Aug. 20, 2020, now Pat. No. 11,478,362.
(Continued)

(51) Int. Cl.
*A61B 34/10* (2016.01)
*A61B 34/20* (2016.01)
(Continued)

(52) U.S. Cl.
CPC ............ *A61F 2/4609* (2013.01); *A61B 34/37* (2016.02); *A61F 2/34* (2013.01); *A61F 2/4684* (2013.01);
(Continued)

(58) Field of Classification Search
None
See application file for complete search history.

(56) References Cited

U.S. PATENT DOCUMENTS

| | | |
|---|---|---|
| 5,769,092 A | 6/1998 | Williamson, Jr. |
| 5,871,018 A | 2/1999 | Delp et al. |
| (Continued) | | |

FOREIGN PATENT DOCUMENTS

| | | |
|---|---|---|
| CN | 107635486 A | 1/2018 |
| JP | 2008-538184 A | 10/2008 |
| (Continued) | | |

OTHER PUBLICATIONS

International Search Report and Written Opinion for International Application No. PCT/US2020/047220, mailed Nov. 19, 2020, 31 pages.

*Primary Examiner* — Thomas E Worden
*Assistant Examiner* — Bryant Tang
(74) *Attorney, Agent, or Firm* — FOLEY & LARDNER LLP

(57) ABSTRACT

A method includes obtaining a surgical plan comprising a first planned position of an implant and a second planned position of an augment relative to a bone. The augment is planned to provide support between the bone and the implant. The method also includes preparing the bone to receive both the implant in the first planned position and the augment in the second planned position by controlling a robotic device based on the first planned position of the implant and the second planned position of the augment.

22 Claims, 21 Drawing Sheets

Related U.S. Application Data

(60) Provisional application No. 62/893,384, filed on Aug. 29, 2019.

(51) Int. Cl.
| | |
|---|---|
| *A61B 34/37* | (2016.01) |
| *A61F 2/30* | (2006.01) |
| *A61F 2/34* | (2006.01) |
| *A61F 2/46* | (2006.01) |
| *A61B 17/17* | (2006.01) |

(52) U.S. Cl.
CPC ..... *A61B 17/1746* (2013.01); *A61B 2034/105* (2016.02); *A61B 2034/107* (2016.02); *A61B 2034/2072* (2016.02); *A61F 2002/30736* (2013.01); *A61F 2002/4633* (2013.01)

(56) References Cited

U.S. PATENT DOCUMENTS

| | | |
|---|---|---|
| 5,961,523 A | 10/1999 | Masini |
| 6,205,411 B1 | 3/2001 | Digioia, III et al. |
| 6,645,196 B1 | 11/2003 | Nixon et al. |
| 6,685,711 B2 | 2/2004 | Axelson et al. |
| 6,917,827 B2 | 7/2005 | Kienzle |
| 7,392,076 B2 | 6/2008 | De La Barrera |
| 7,477,926 B2 | 1/2009 | McCombs |
| 7,594,933 B2 | 9/2009 | Kammerzell et al. |
| 7,780,681 B2 | 8/2010 | Sarin et al. |
| 7,835,778 B2 | 11/2010 | Foley et al. |
| 7,927,338 B2 | 4/2011 | Laffargue et al. |
| 7,932,825 B2 | 4/2011 | Berger |
| 8,010,180 B2 | 8/2011 | Quaid et al. |
| 8,249,318 B2 | 8/2012 | Schmitt et al. |
| 8,337,426 B2 | 12/2012 | Nycz |
| 8,337,508 B2 | 12/2012 | Lavallee et al. |
| 8,382,765 B2 | 2/2013 | Axelson et al. |
| 8,400,312 B2 | 3/2013 | Hotokebuchi et al. |
| 8,449,551 B2 | 5/2013 | Amiot et al. |
| 8,454,609 B2 | 6/2013 | Petit et al. |
| 8,498,744 B2 | 7/2013 | Odermatt et al. |
| 8,506,645 B2 | 8/2013 | Blaylock et al. |
| 8,512,346 B2 | 8/2013 | Couture |
| 8,556,074 B2 | 10/2013 | Turner et al. |
| 8,603,093 B2 | 12/2013 | Hakki |
| 8,660,331 B2 | 2/2014 | Fernandez Dell Oca |
| 8,709,016 B2 | 4/2014 | Park et al. |
| 8,731,253 B2 | 5/2014 | Dardenne et al. |
| 8,753,346 B2 | 6/2014 | Suarez et al. |
| 8,774,900 B2 | 7/2014 | Buly et al. |
| 8,861,818 B2 | 10/2014 | Ito et al. |
| 8,891,847 B2 | 11/2014 | Helm et al. |
| 8,979,859 B2 | 3/2015 | Leparmentier et al. |
| 8,992,542 B2 | 3/2015 | Hagag et al. |
| 8,998,797 B2 | 4/2015 | Omori |
| 8,998,910 B2 | 4/2015 | Borja et al. |
| 9,017,335 B2 | 4/2015 | Stiehl |
| 9,031,284 B2 | 5/2015 | Spath |
| 9,044,173 B2 | 6/2015 | Crouch |
| 9,125,669 B2 | 9/2015 | Ranawat et al. |
| 9,125,702 B2 | 9/2015 | Witt |
| 9,179,983 B2 | 11/2015 | Heavener et al. |
| 9,220,510 B2 | 12/2015 | Cheal et al. |
| 9,247,998 B2 | 2/2016 | Hladio et al. |
| 9,345,552 B2 | 5/2016 | Janik et al. |
| 9,402,726 B2 | 8/2016 | Linderman et al. |
| 9,408,617 B2 | 8/2016 | Ranawat et al. |
| 9,427,320 B2 | 8/2016 | Meridew |
| 9,456,765 B2 | 10/2016 | Odermatt et al. |
| 9,588,583 B2 | 3/2017 | Lightcap et al. |
| 9,668,867 B2 | 6/2017 | Kelley |
| 9,675,273 B2 | 6/2017 | Gluncic |
| 9,713,539 B2 | 7/2017 | Haimerl et al. |
| 9,763,747 B2 | 9/2017 | Kang et al. |
| 9,775,681 B2 | 10/2017 | Quaid et al. |
| 9,808,261 B2 | 11/2017 | Gelaude et al. |
| 9,877,793 B2 | 1/2018 | Bonutti |
| 9,949,797 B2 | 4/2018 | Meridew et al. |
| 9,955,983 B2 | 5/2018 | Aghazadeh |
| 9,955,984 B2 | 5/2018 | Winslow et al. |
| 10,010,377 B2 | 7/2018 | Iorgulescu et al. |
| 10,052,166 B2 | 8/2018 | Ziaei et al. |
| 10,070,903 B2 | 9/2018 | Blau |
| 10,085,804 B2 | 10/2018 | Nortman et al. |
| 10,206,688 B2 | 2/2019 | Park et al. |
| 10,231,739 B1 | 3/2019 | Bonutti |
| 10,231,790 B2 | 3/2019 | Quaid et al. |
| 10,265,127 B2 | 4/2019 | Jaramaz et al. |
| 10,265,193 B2 | 4/2019 | Sherman et al. |
| 10,271,886 B2 | 4/2019 | Abiven |
| 10,285,683 B2 | 5/2019 | Plaskos et al. |
| 10,314,666 B2 | 6/2019 | Aghazadeh |
| 10,321,961 B2 | 6/2019 | McCarthy et al. |
| 10,327,904 B2 | 6/2019 | Otto et al. |
| 10,363,149 B2 | 7/2019 | Van Der Walt et al. |
| 10,390,966 B2 | 8/2019 | Clary et al. |
| 10,398,514 B2 | 9/2019 | Ryan et al. |
| 10,405,910 B2 | 9/2019 | Netravali et al. |
| 10,456,205 B2 | 10/2019 | Meridew et al. |
| 10,463,415 B2 | 11/2019 | Walter et al. |
| 10,470,821 B2 | 11/2019 | Jaramaz et al. |
| 10,478,318 B2 | 11/2019 | Behzadi et al. |
| 10,485,450 B2 | 11/2019 | Gupta et al. |
| 10,499,996 B2 | 12/2019 | De Almeida |
| 10,603,115 B2 | 3/2020 | Van Der Walt et al. |
| 10,660,709 B2 | 5/2020 | Chaoui |
| 10,675,063 B2 | 6/2020 | Pavlovskaia et al. |
| 10,695,183 B2 | 6/2020 | Nelson |
| 10,716,580 B2 | 7/2020 | Berend et al. |
| 10,716,628 B2 | 7/2020 | McCabe et al. |
| 10,716,630 B2 | 7/2020 | Krebs et al. |
| 10,729,558 B2 | 8/2020 | Macke et al. |
| 10,765,384 B2 | 9/2020 | Wollowick et al. |
| 10,772,685 B2 | 9/2020 | Erbe |
| 10,786,312 B2 | 9/2020 | Fanson et al. |
| 10,806,529 B2 | 10/2020 | Timperley et al. |
| 10,806,541 B2 | 10/2020 | Ross |
| 10,806,591 B2 | 10/2020 | Kovacs et al. |
| 10,863,995 B2 | 12/2020 | Nielsen et al. |
| 10,881,462 B2 | 1/2021 | Heavener et al. |
| 10,881,470 B2 | 1/2021 | Falardeau et al. |
| 10,932,866 B1 | 3/2021 | Bonny et al. |
| 10,945,801 B2 | 3/2021 | Borus et al. |
| 10,973,590 B2 | 4/2021 | Boddington et al. |
| 10,980,645 B2 | 4/2021 | Falardeau et al. |
| 10,991,070 B2 | 4/2021 | Saget et al. |
| 11,020,053 B2 | 6/2021 | Bailey et al. |
| 11,020,189 B2 | 6/2021 | Tao et al. |
| 11,026,811 B2 | 6/2021 | Sherman et al. |
| 11,071,596 B2 | 7/2021 | Ryan et al. |
| 11,160,609 B2 | 11/2021 | Otto et al. |
| 11,172,990 B2 | 11/2021 | Lang |
| 11,173,048 B2 | 11/2021 | Yadav et al. |
| 11,176,667 B2 | 11/2021 | Hladio et al. |
| 11,179,062 B2 | 11/2021 | Borja |
| 11,179,167 B2 | 11/2021 | Stone |
| 11,207,134 B2 | 12/2021 | Hafez et al. |
| 11,207,195 B2 | 12/2021 | Bushell et al. |
| 11,213,336 B2 | 1/2022 | Walter et al. |
| 11,229,519 B2 | 1/2022 | Radermacher et al. |
| 11,229,520 B2 | 1/2022 | Fanson et al. |
| 11,234,825 B2 | 2/2022 | Johannaber et al. |
| 11,241,285 B2 | 2/2022 | Viscardi et al. |
| 11,241,287 B2 | 2/2022 | Boettner |
| 11,259,816 B2 | 3/2022 | Otto et al. |
| 11,298,188 B2 | 4/2022 | Kehres et al. |
| 11,298,189 B2 | 4/2022 | Kelman et al. |
| 11,298,190 B2 | 4/2022 | Quaid, III |
| 11,311,339 B2 | 4/2022 | Jansen et al. |
| 11,351,007 B1 | 6/2022 | Meftah et al. |
| 11,369,437 B2 | 6/2022 | Walter et al. |
| 11,386,556 B2 | 7/2022 | Saget et al. |
| 11,413,095 B2 | 8/2022 | Hladio et al. |
| 11,432,945 B2 | 9/2022 | Viscardi et al. |

(56) References Cited

U.S. PATENT DOCUMENTS

| | | |
|---|---|---|
| 11,452,566 B2 | 9/2022 | Michael et al. |
| 11,464,574 B2 | 10/2022 | Haider et al. |
| 11,478,310 B2 | 10/2022 | Poltaretskyi et al. |
| 11,478,362 B2 | 10/2022 | Thompson et al. |
| 11,484,325 B2 | 11/2022 | Hafez et al. |
| 11,484,368 B2 | 11/2022 | Krebs et al. |
| 11,490,965 B2 | 11/2022 | Bischoff et al. |
| 11,534,185 B2 | 12/2022 | Dumpe et al. |
| 11,576,725 B2 | 2/2023 | Chav et al. |
| 11,602,395 B2 | 3/2023 | Lang |
| 11,602,443 B1 | 3/2023 | Cole et al. |
| 11,607,233 B2 | 3/2023 | Tikka |
| 11,612,503 B1 | 3/2023 | Cole et al. |
| 11,622,813 B2 | 4/2023 | Ferro et al. |
| 11,622,814 B2 | 4/2023 | Dees et al. |
| 11,622,862 B2 | 4/2023 | Van Der Wal et al. |
| 11,642,174 B2 | 5/2023 | Wollowick et al. |
| 11,666,447 B1 | 6/2023 | Trauner et al. |
| 11,678,992 B2 | 6/2023 | Servidio et al. |
| 11,690,682 B2 | 7/2023 | Wilkinson et al. |
| 11,701,182 B2 | 7/2023 | McCabe et al. |
| 11,707,333 B2 | 7/2023 | Merette et al. |
| 11,717,353 B2 | 8/2023 | Zuhars et al. |
| 11,730,601 B2 | 8/2023 | Beck et al. |
| 11,730,603 B2 | 8/2023 | Zappacosta et al. |
| 11,737,826 B2 | 8/2023 | De Souza et al. |
| 11,737,893 B2 | 8/2023 | Schipper et al. |
| 11,744,644 B2 | 9/2023 | Wilkinson et al. |
| 11,744,650 B2 | 9/2023 | Mahfouz |
| 11,771,504 B2 | 10/2023 | Kang et al. |
| 11,786,284 B2 | 10/2023 | Khosla et al. |
| 11,806,239 B2 | 11/2023 | Macke |
| 11,813,052 B2 | 11/2023 | Gupta et al. |
| 11,819,298 B2 | 11/2023 | Librot |
| 11,986,255 B2 | 5/2024 | Bonny et al. |
| 11,998,280 B2 | 6/2024 | Chav et al. |
| 2002/0133162 A1 | 9/2002 | Axelson, Jr. et al. |
| 2005/0101966 A1 | 5/2005 | Lavallee |
| 2005/0148855 A1 | 7/2005 | Kienzle, III |
| 2005/0182320 A1 | 8/2005 | Stifter et al. |
| 2005/0187562 A1 | 8/2005 | Grimm et al. |
| 2008/0033571 A1 | 2/2008 | Tuke |
| 2008/0065085 A1 | 3/2008 | Couture et al. |
| 2009/0234217 A1 | 9/2009 | Mire et al. |
| 2010/0217400 A1* | 8/2010 | Nortman ............... A61B 34/25 623/20.14 |
| 2011/0016690 A1 | 1/2011 | Narainasamy et al. |
| 2012/0190971 A1 | 7/2012 | De Wekker |
| 2013/0105577 A1 | 5/2013 | Hildreth et al. |
| 2013/0144352 A1 | 6/2013 | Axelson et al. |
| 2013/0144570 A1 | 6/2013 | Axelson et al. |
| 2014/0031664 A1 | 1/2014 | Kang et al. |
| 2014/0135773 A1 | 5/2014 | Stein et al. |
| 2015/0119987 A1 | 4/2015 | Davignon et al. |
| 2016/0038161 A1 | 2/2016 | Gibson |
| 2016/0193051 A1 | 7/2016 | Budhabhatti et al. |
| 2016/0278868 A1 | 9/2016 | Berend et al. |
| 2017/0065432 A1 | 3/2017 | Singh |
| 2017/0161434 A1 | 6/2017 | Naudi |
| 2017/0215967 A1 | 8/2017 | Spath |
| 2017/0348011 A1 | 12/2017 | Kourtis et al. |
| 2017/0360509 A1 | 12/2017 | Bonny et al. |
| 2018/0000547 A1 | 1/2018 | Kang et al. |
| 2018/0344465 A1 | 12/2018 | McPherson et al. |
| 2019/0000561 A1 | 1/2019 | Decker et al. |
| 2019/0090952 A1 | 3/2019 | Bonny et al. |
| 2019/0105108 A1* | 4/2019 | Bonny .................. A61B 34/20 |
| 2019/0175283 A1 | 6/2019 | Bonny et al. |
| 2019/0231432 A1 | 8/2019 | Amanatullah |
| 2019/0365481 A1 | 12/2019 | Otto et al. |
| 2019/0380792 A1 | 12/2019 | Poltaretskyi et al. |
| 2020/0000527 A1 | 1/2020 | Cazal |
| 2020/0060766 A1 | 2/2020 | Hafez et al. |
| 2020/0074631 A1 | 3/2020 | Giancardo et al. |
| 2020/0077924 A1 | 3/2020 | Hladio et al. |
| 2020/0129311 A1 | 4/2020 | Singh et al. |
| 2020/0163721 A1 | 5/2020 | Aghazadeh |
| 2020/0222206 A1 | 7/2020 | Elliot |
| 2020/0281656 A1 | 9/2020 | Torabi et al. |
| 2020/0352654 A1 | 11/2020 | Van Der Walt et al. |
| 2020/0383796 A1 | 12/2020 | Johannaber et al. |
| 2020/0383803 A1 | 12/2020 | Wu et al. |
| 2021/0022808 A1 | 1/2021 | Lang |
| 2021/0038328 A1 | 2/2021 | Boisvert et al. |
| 2021/0052327 A1 | 2/2021 | Kuznik et al. |
| 2021/0059838 A1 | 3/2021 | Bodner |
| 2021/0093389 A1 | 4/2021 | Poltaretskyi et al. |
| 2021/0093390 A1 | 4/2021 | Poltaretskyi et al. |
| 2021/0128249 A1 | 5/2021 | Billard et al. |
| 2021/0145517 A1 | 5/2021 | Pierrepont et al. |
| 2021/0161681 A1 | 6/2021 | Nguyen et al. |
| 2021/0220054 A1 | 7/2021 | Parker et al. |
| 2021/0275227 A1 | 9/2021 | Park et al. |
| 2021/0327065 A1 | 10/2021 | Wright |
| 2022/0008131 A1 | 1/2022 | Sculco et al. |
| 2022/0031414 A1 | 2/2022 | Wright et al. |
| 2022/0039881 A1 | 2/2022 | Avisar et al. |
| 2022/0104881 A1 | 4/2022 | Otto et al. |
| 2022/0117755 A1 | 4/2022 | McGuan et al. |
| 2022/0125518 A1 | 4/2022 | Signoretti et al. |
| 2022/0160439 A1 | 5/2022 | Ryan et al. |
| 2022/0160440 A1 | 5/2022 | Jaramaz et al. |
| 2022/0175400 A1 | 6/2022 | Greber |
| 2022/0175453 A1 | 6/2022 | Xu et al. |
| 2022/0183757 A1 | 6/2022 | Caldera et al. |
| 2022/0192755 A1 | 6/2022 | Siccardi et al. |
| 2022/0202494 A1 | 6/2022 | Dressler et al. |
| 2022/0202503 A1 | 6/2022 | Dressler et al. |
| 2022/0218422 A1 | 7/2022 | Khurana et al. |
| 2022/0257145 A1 | 8/2022 | Hladio et al. |
| 2022/0273281 A1* | 9/2022 | McKinnon ........... A61B 17/025 |
| 2022/0296259 A1 | 9/2022 | Shah |
| 2022/0313443 A1 | 10/2022 | Keefer et al. |
| 2022/0323162 A1 | 10/2022 | Bonny et al. |
| 2022/0361955 A1 | 11/2022 | Signoretti et al. |
| 2022/0398817 A1 | 12/2022 | Chaoui et al. |
| 2023/0010852 A1 | 1/2023 | Cooper et al. |
| 2023/0013210 A1 | 1/2023 | Facchinello et al. |
| 2023/0056596 A1 | 2/2023 | Farley et al. |
| 2023/0068971 A1 | 3/2023 | Derouault et al. |
| 2023/0113848 A1 | 4/2023 | Chaoui et al. |
| 2023/0116074 A1 | 4/2023 | Grostefon et al. |
| 2023/0126955 A1 | 4/2023 | Jaramaz et al. |
| 2023/0131309 A1 | 4/2023 | Jaramaz et al. |
| 2023/0141368 A1 | 5/2023 | Donnelly et al. |
| 2023/0146371 A1 | 5/2023 | Gargac et al. |
| 2023/0157756 A1 | 5/2023 | Simoes et al. |
| 2023/0190139 A1 | 6/2023 | Godbey et al. |
| 2023/0190494 A1 | 6/2023 | Webb et al. |
| 2023/0200826 A1 | 6/2023 | McAuliffe |
| 2023/0240759 A1 | 8/2023 | Khare |
| 2023/0255691 A1 | 8/2023 | Blau et al. |
| 2023/0285080 A1 | 9/2023 | Hladio et al. |
| 2023/0285082 A1 | 9/2023 | Grammatopoulos et al. |
| 2023/0301719 A1 | 9/2023 | Murphy |

FOREIGN PATENT DOCUMENTS

| | | | |
|---|---|---|---|
| JP | 2017-535406 A | 11/2017 | |
| JP | 2018-519876 A | 7/2018 | |
| JP | 2019-523049 A | 8/2019 | |
| WO | WO-2016/089870 A1 | 6/2016 | |
| WO | WO-2016/187290 A1 | 11/2016 | |
| WO | WO-2017/204832 A1 | 11/2017 | |
| WO | WO-2018/013848 A1 | 1/2018 | |
| WO | WO-2018/125834 A1 | 7/2018 | |
| WO | WO-2018/169995 A1 | 9/2018 | |
| WO | WO-2019/148154 A1 | 8/2019 | |
| WO | WO-2019/202320 A1 | 10/2019 | |
| WO | WO-2020/231656 A2 | 11/2020 | |
| WO | WO-2020186194 A9 * | 11/2020 | ............ A61B 34/10 |
| WO | WO-2021003275 A1 * | 1/2021 | ............ A61B 34/10 |
| WO | WO-2022/126827 A1 | 6/2022 | |
| WO | WO-2022/126828 A1 | 6/2022 | |

(56) References Cited

FOREIGN PATENT DOCUMENTS

| WO | WO-2022/173775 A1 | 8/2022 |
| WO | WO-2022/183719 A1 | 9/2022 |
| WO | WO-2023/059931 A1 | 4/2023 |
| WO | WO-2023/165568 A1 | 9/2023 |
| WO | WO-2023/197504 A1 | 10/2023 |
| WO | WO-2023/214036 A1 | 11/2023 |

* cited by examiner

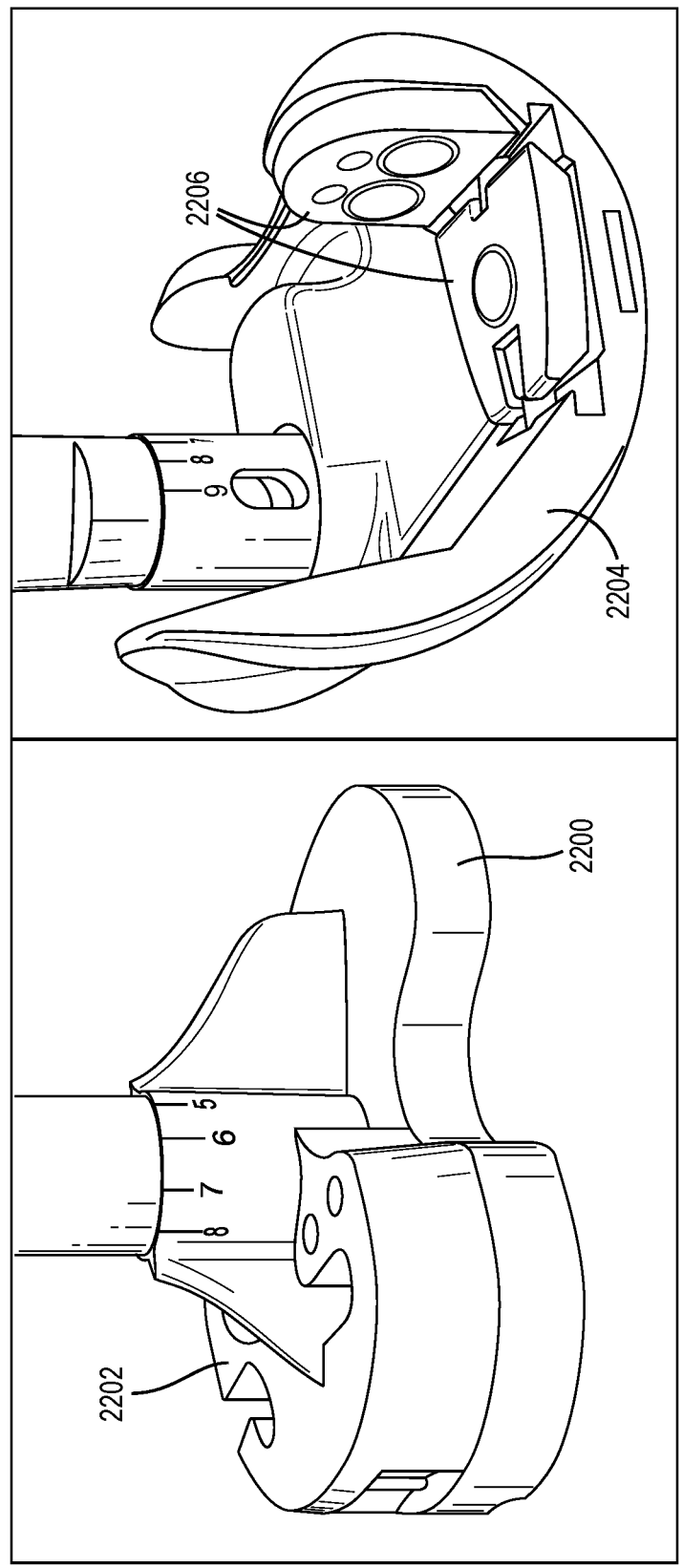

ROBOTIC SURGERY SYSTEM FOR AUGMENTED ARTHROPLASTY PROCEDURES

CROSS-REFERENCE TO RELATED APPLICATIONS

This application is a continuation of U.S. application Ser. No. 17/257,162, filed Dec. 30, 2020, which is a national phase application of PCT Application No. PCT/US2020/047220, filed Aug. 20, 2020, which claims the benefit of and priority to U.S. Provisional Application No. 62/893,384 filed Aug. 29, 2019. The entire disclosures of the above-referenced applications are incorporated by reference herein.

BACKGROUND

The present disclosure relates generally to surgical systems for orthopedic surgeries, and more particularly to surgical systems for total and partial hip arthroplasty procedures. Hip arthroplasty, colloquially referred to as hip replacement, is widely used to treat hip osteoarthritis and other damage to a patient's hip joint by replacing portions of the hip anatomy with prosthetic components.

One possible tool for use in total hip arthroplasty procedure is a robotically-assisted surgical system. A robotically-assisted surgical system typically includes a robotic device that is used to prepare a patient's anatomy, a tracking system configured to monitor the location of the robotic device relative to the patient's anatomy, and a computing system configured to monitor and control the robotic device. Robotically-assisted surgical systems, in various forms, autonomously carry out surgical tasks, provide force feedback to a user manipulating a surgical device to complete surgical tasks, augment surgeon dexterity and precision, and/or provide other navigational cues to facilitate safe and accurate surgical operations.

A surgical plan is typically established prior to performing a surgical procedure with a robotically-assisted surgical system. Based on the surgical plan, the surgical system guides, controls, or limits movements of the surgical tool during portions of the surgical procedure. Guidance and/or control of the surgical tool serves to protect the patient and to assist the surgeon during implementation of the surgical plan.

SUMMARY

One implementation of the present disclosure is a system for facilitating arthroplasty procedures. The system includes a robotic device, a reaming tool configured to interface with the robotic device, and a processing circuit communicable with the robotic device. The processing circuit is configured to obtain a surgical plan comprising a first planned position of an implant cup and a second planned position of an implant augment relative to a bone of a patient, determine a planned bone modification configured to prepare the bone to receive the implant cup in the first planned position and the implant augment in the second planned position, generate one or more virtual objects based on the planned bone modification, control the robotic device to constrain the cutting tool with the one or more virtual objects while the cutting tool interfaces with the robotic device and is operated to modify the bone in accordance with the planned bone modification.

Another implementation of the present disclosure is a method. The method includes obtaining a surgical plan including a first planned position of an implant cup and a second planned position of an implant augment relative to a bone of a patient, determining a planned bone modification configured to prepare the bone to receive the implant cup in the first planned position and the implant augment in the second planned position, generating one or more virtual objects based on the planned bone modification, and controlling a robotic device using the one or more virtual objects to facilitate modification of the bone with a surgical tool interfacing with the robotic device in accordance with the planned bone modification.

BRIEF DESCRIPTION OF THE DRAWINGS

FIG. 22 is a perspective view of a tibial implant and a tibial augment, according to an exemplary embodiment.

FIG. 23 is a perspective view of a femoral implant and a pair of femoral augments, according to an exemplary embodiment.

DETAILED DESCRIPTION

Figure 1A:
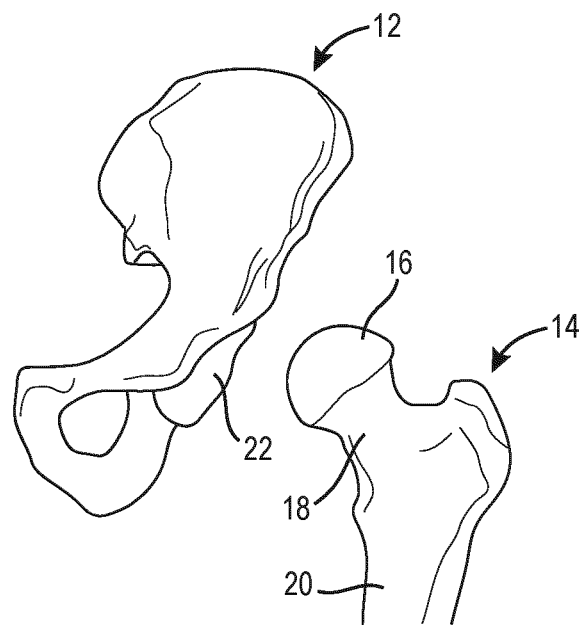
FIG. 1A is a perspective view of a femur and a pelvis.

Presently preferred embodiments of the invention are illustrated in the drawings. An effort has been made to use the same or like reference numbers throughout the drawings to refer to the same or like parts. Although this specification refers primarily to a robotic arm for orthopedic hip replacement, it should be understood that the subject matter described herein is applicable to other types of robotic systems, including those used for surgical and non-surgical applications, as well as to other joints of the body, such as, for example, a knee or shoulder joint.

Figure 1B:
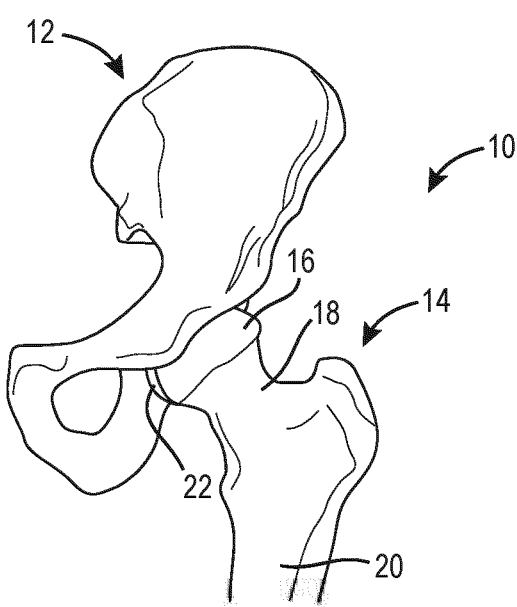
FIG. 1B is a perspective view of a hip joint formed by the femur and pelvis of FIG. 1A.

The hip joint is the joint between the femur and the pelvis and primarily functions to support the weight of the body in static (for example, standing) and dynamic (for example, walking) postures. FIG. 1A illustrates the bones of a hip joint 10, which include a pelvis 12 (shown in part) and a proximal end of a femur 14. The proximal end of the femur 14 includes a femoral head 16 disposed on a femoral neck 18. The femoral neck 18 connects the femoral head 16 to a femoral shaft 20. As shown in FIG. 1B, the femoral head 16 fits into a concave socket in the pelvis 12 called the acetabulum 22, thereby forming the hip joint 10. The acetabulum 22 and femoral head 16 are both covered by articular cartilage that absorbs shock and promotes articulation of the joint 10.

Figure 1C:
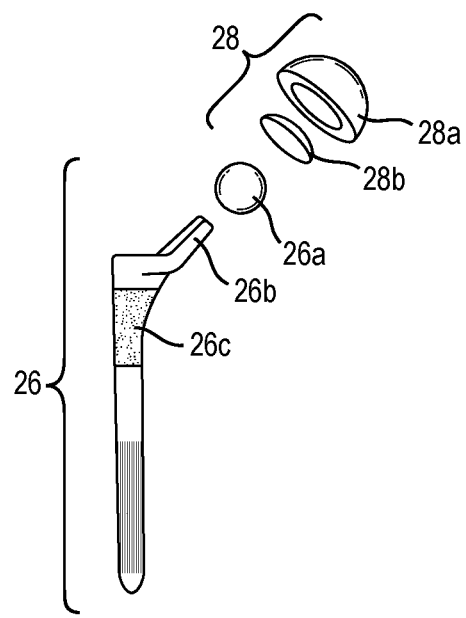
FIG. 1C is an exploded perspective view of a femoral component and an acetabular component for a total hip replacement procedure.
Figure 1D:
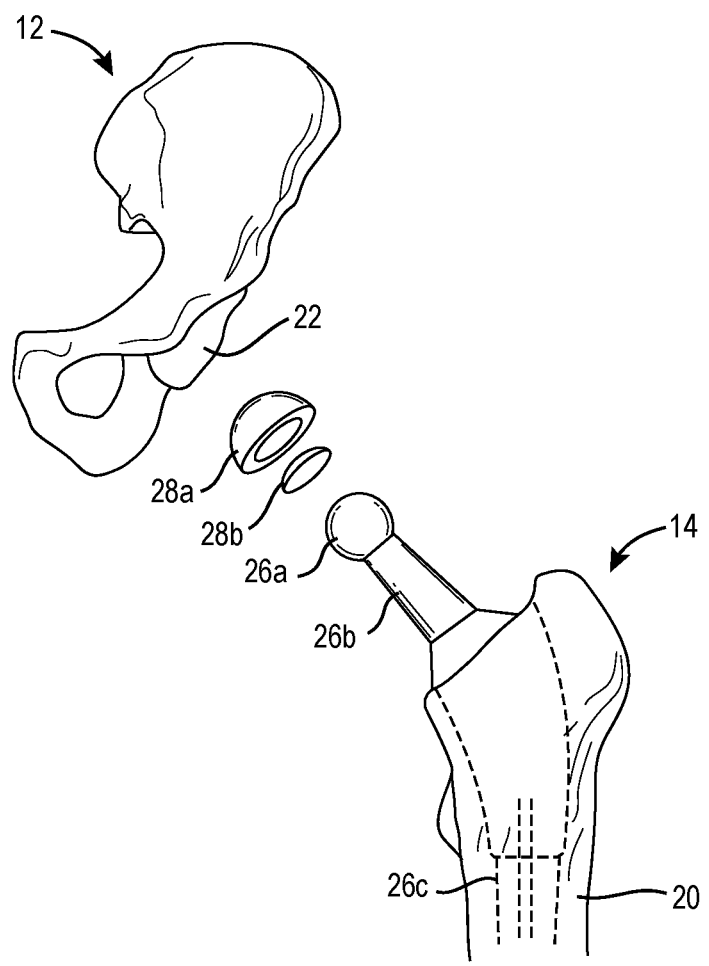
FIG. 1D is a perspective view illustrating placement of the femoral component and acetabular component of FIG. 1C in relation to the femur and pelvis of FIG. 1A, respectively.

Over time, the hip joint 10 may degenerate (for example, due to osteoarthritis) resulting in pain and diminished functionality. As a result, a hip replacement procedure, such as total hip arthroplasty or hip resurfacing, may be necessary. During hip replacement, a surgeon replaces portions of a patient's hip joint 10 with artificial components. In total hip arthroplasty, the surgeon removes the femoral head 16 and neck 18 and replaces the natural bone with a prosthetic femoral component 26 comprising a head 26a, a neck 26b, and a stem 26c (shown in FIG. 1C). As shown in FIG. 1D, the stem 26c of the femoral component 26 is anchored in a cavity the surgeon creates in the intramedullary canal of the femur 14. Alternatively, if disease is confined to the surface of the femoral head 16, the surgeon may opt for a less invasive approach in which the femoral head is resurfaced (e.g., using a cylindrical reamer) and then mated with a prosthetic femoral head cup (not shown).

Similarly, if the natural acetabulum 22 of the pelvis 12 is worn or diseased, the surgeon resurfaces the acetabulum 22 using a reamer and replaces the natural surface with a prosthetic acetabular component 28 comprising a hemispherical shaped cup 28a (shown in FIG. 1C) that may include a liner 28b. To install the acetabular component 28, the surgeon connects the cup 28a to a distal end of an impactor tool and implants the cup 28a into the reamed acetabulum 22 by repeatedly striking a proximal end of the impactor tool with a mallet. If the acetabular component 28 includes a liner 28b, the surgeon snaps the liner 28b into the cup 28a after implanting the cup 28a. Depending on the position in which the surgeon places the patient for surgery, the surgeon may use a straight or offset reamer to ream the acetabulum 22 and a straight or offset impactor to implant the acetabular cup 28a. For example, a surgeon that uses a postero-lateral approach may prefer straight reaming and impaction whereas a surgeon that uses an antero-lateral approach may prefer offset reaming and impaction.

In some cases, an implant augment is used to support or otherwise facilitate reconstruction of the acetabulum 22 to facilitate fixation of the cup 28a to the pelvis 12 in a preferred position and orientation. Use of an augment may be preferable in several scenarios. As one example, an implant augment may be advantageous post-traumatic hip reconstructions, in which a traumatic injury (e.g., car crash, etc.) caused damage to the pelvis 12. As another example, an implant augment may be advantageous in cases of hip dysplasia or other cases of acetabular bone loss, i.e., to fill space created by such bone loss. As another example, an implant augment may be advantageous for revision hip arthroplasty procedures, in which a previously-implanted hip prosthesis is removed and replaced with a new implant due to degradation of neighboring bone or other complications.

Current surgical procedures that involve implant augments typically rely on surgeon expertise and experience to manually place an implant augment in a position that looks and feels correct to the surgeon intraoperatively. Such procedures may be difficult and result in extended surgical time. Additionally, currently-available robotically-assisted surgical devices for hip arthroplasty do not provide for placement of implant augments. The systems and methods described herein provide for computer-assisted planning of implant placement and robotically-assisted surgical steps to facilitate bone preparation for implant augments and placement of implant augments during hip arthroplasty procedures, thereby facilitating hip arthroplasty procedures in cases of bone loss, traumatic injury, revision hip replacements, or other relevant scenarios. The systems and methods described herein may thereby improve patient outcomes, reduce surgery times, and reduce the burden on surgeons for augmented hip arthroplasty procedures.

Figure 2:
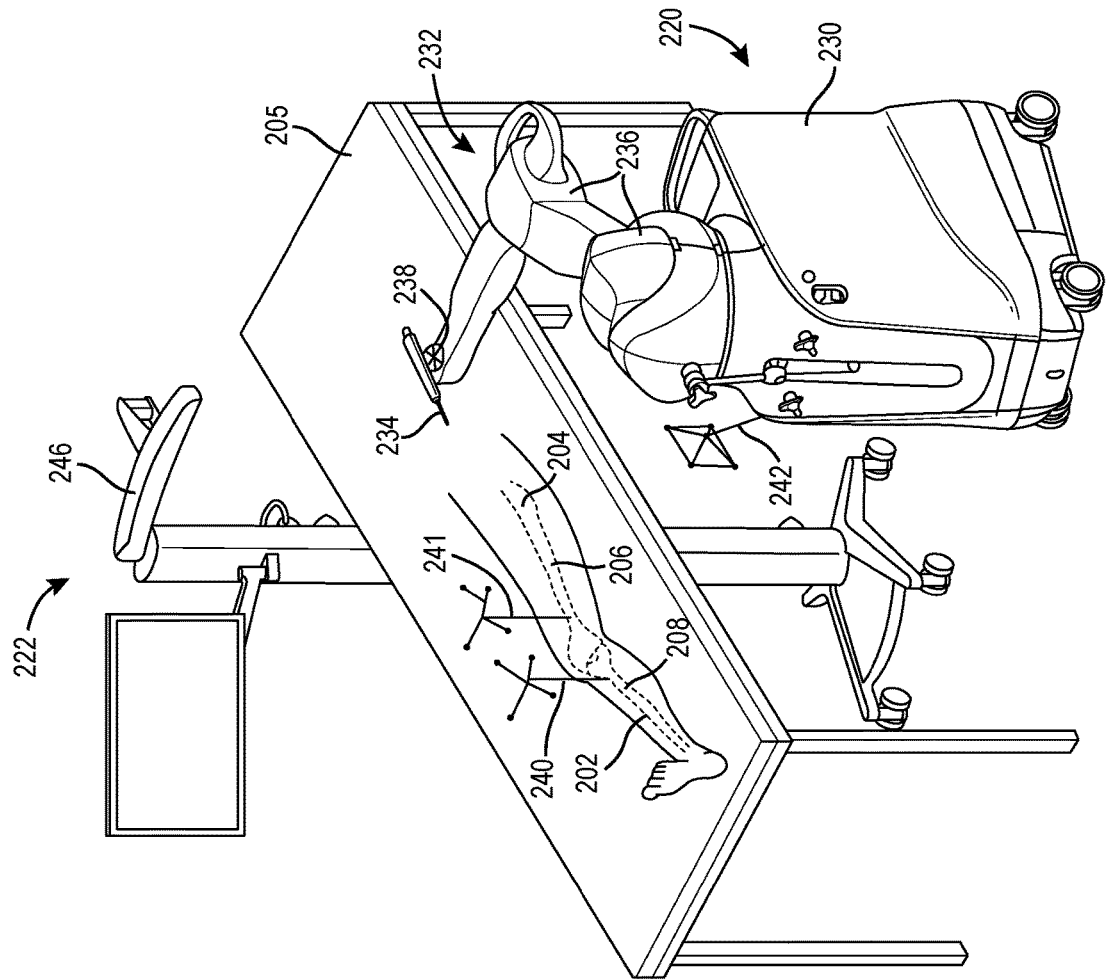
FIG. 2 is an illustration of a surgical system, according to an exemplary embodiment.
Figure 2:
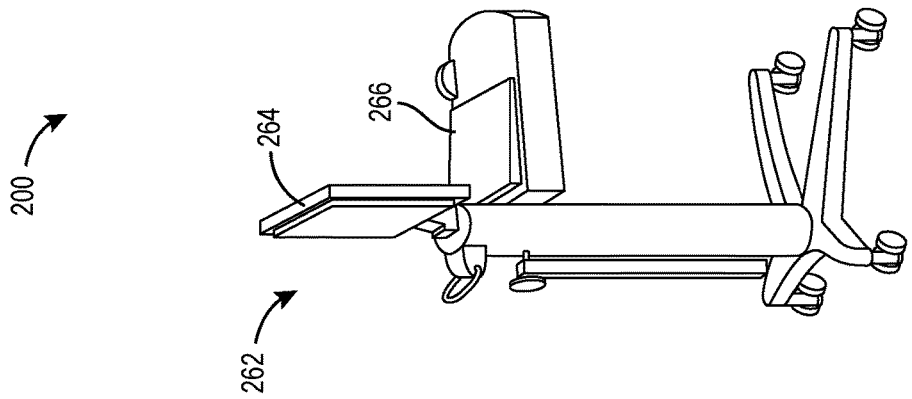

Referring now to FIG. 2, a surgical system 200 for orthopedic surgery is shown, according to an exemplary embodiment. In general, the surgical system 200 is configured to facilitate the planning and execution of a surgical plan, for example to facilitate a joint-related procedure. As shown in FIG. 2, the surgical system 200 is set up to treat a leg 202 of a patient 204 sitting or lying on table 205. In the illustration shown in FIG. 2, the leg 202 includes femur 206 and tibia 208, between which a prosthetic knee implant is to be implanted in a total knee arthroscopy procedure. The scenario shown in FIG. 2 may correspond to the description below with reference to FIGS. 17-22. In other scenarios, for example as described herein with reference to 1A-1D and FIGS. 3-16, the surgical system 200 is set up to treat the hip 10 of a patient, i.e., the femur 14 and the pelvis 12 of the patient (illustrated in FIGS. 1A-1D). Additionally, in still other scenarios, the surgical system 200 is set up to treat a shoulder of a patient, i.e., to facilitate replacement and/or augmentation of components of a shoulder joint (e.g., to facilitate placement of a humeral component, a glenoid component, and a graft or implant augment). Various other anatomical regions and procedures are also possible. To facilitate the procedure, surgical system 200 includes robotic device 220, tracking system 222, and computing system 224.

The robotic device 220 is configured to modify a patient's anatomy (e.g., femur 206 of patient 204) under the control of the computing system 224. One embodiment of the robotic device 220 is a haptic device. "Haptic" refers to a sense of touch, and the field of haptics relates to, among other things, human interactive devices that provide feedback to an operator. Feedback may include tactile sensations such as, for example, vibration. Feedback may also include providing force to a user, such as a positive force or a resistance to movement. One use of haptics is to provide a user of the device with guidance or limits for manipulation of that device. For example, a haptic device may be coupled to a surgical tool, which can be manipulated by a surgeon to perform a surgical procedure. The surgeon's manipulation of the surgical tool can be guided or limited through the use of haptics to provide feedback to the surgeon during manipulation of the surgical tool.

Another embodiment of the robotic device 220 is an autonomous or semi-autonomous robot. "Autonomous" refers to a robotic device's ability to act independently or semi-independently of human control by gathering information about its situation, determining a course of action, and automatically carrying out that course of action. For example, in such an embodiment, the robotic device 220, in communication with the tracking system 222 and the computing system 224, may autonomously complete the series of femoral cuts mentioned above without direct human intervention.

The robotic device 220 includes a base 230, a robotic arm 232, and a surgical tool 234, and is communicably coupled to the computing system 224 and the tracking system 222. The base 230 provides a moveable foundation for the robotic arm 232, allowing the robotic arm 232 and the surgical tool 234 to be repositioned as needed relative to the patient 204 and the table 205. The base 230 may also contain power systems, computing elements, motors, and other electronic or mechanical system necessary for the functions of the robotic arm 232 and the surgical tool 234 described below.

The robotic arm 232 is configured to support the surgical tool 234 and provide a force as instructed by the computing system 224. In some embodiments, the robotic arm 232 allows a user to manipulate the surgical tool and provides force feedback to the user. In such an embodiment, the robotic arm 232 includes joints 236 and mount 238 that include motors, actuators, or other mechanisms configured to allow a user to freely translate and rotate the robotic arm 232 and surgical tool 234 through allowable poses while providing force feedback to constrain or prevent some movements of the robotic arm 232 and surgical tool 234 as instructed by computing system 224. As described in detail below, the robotic arm 232 thereby allows a surgeon to have full control over the surgical tool 234 within a control object while providing force feedback along a boundary of that object (e.g., a vibration, a force preventing or resisting penetration of the boundary). In some embodiments, the robotic arm is configured to move the surgical tool to a new pose automatically without direct user manipulation, as instructed by computing system 224, in order to position the robotic arm as needed and/or complete certain surgical tasks, including, for example, cuts in a femur 206 or an acetabulum.

The surgical tool 234 is configured to cut, burr, grind, drill, partially resect, reshape, and/or otherwise modify a bone. The surgical tool 234 may be any suitable tool, and may be one of multiple tools interchangeably connectable to robotic device 220. For example, as shown in FIG. 2 the surgical tool 234 is a spherical burr. The surgical tool may also be a sagittal saw, for example with a blade aligned parallel with a tool axis or perpendicular to the tool axis. The surgical tool 234 may also be a holding arm or other support configured to hold an implant component (e.g., cup 28a, implant augment, etc.) in position while the implant component is screwed to a bone, adhered (e.g., cemented) to a bone or other implant component, or otherwise installed in a preferred position. In some embodiments, the surgical tool 234 is an impaction tool configured to provide an impaction force to a cup 28a to facilitate fixation of the cup 28a to a pelvis 12 in a planned location and orientation.

Tracking system 222 is configured to track the patient's anatomy (e.g., femur 206 and tibia 208) and the robotic device 220 (i.e., surgical tool 234 and/or robotic arm 232) to enable control of the surgical tool 234 coupled to the robotic arm 232, to determine a position and orientation of modifications or other results made by the surgical tool 234, and allow a user to visualize the bones (e.g., femur 206, the tibia 208, pelvis 12, humerus, scapula, etc. as applicable in various procedures), the surgical tool 234, and/or the robotic arm 232 on a display of the computing system 224. More particularly, the tracking system 222 determines a position and orientation (i.e., pose) of objects (e.g., surgical tool 234, femur 206) with respect to a coordinate frame of reference and tracks (i.e., continuously determines) the pose of the objects during a surgical procedure. According to various embodiments, the tracking system 222 may be any type of navigation system, including a non-mechanical tracking system (e.g., an optical tracking system), a mechanical tracking system (e.g., tracking based on measuring the relative angles of joints 236 of the robotic arm 232), or any combination of non-mechanical and mechanical tracking systems.

In the embodiment shown in FIG. 2, the tracking system 222 includes an optical tracking system. Accordingly, tracking system 222 includes a first fiducial tree 240 coupled to the tibia 208, a second fiducial tree 241 coupled to the femur 206, a third fiducial tree 242 coupled to the base 230, one or more fiducials coupled to surgical tool 234, and a detection device 246 configured to detect the three-dimensional position of fiducials (i.e., markers on fiducial trees 240-242). Fiducial trees 240, 241 may be coupled to other bones as suitable for various procedures (e.g., pelvis 12 and femur 206 in a hip arthroplasty procedure). Detection device 246 may be an optical detector such as a camera or infrared sensor. The fiducial trees 240-242 include fiducials, which are markers configured to show up clearly to the optical detector and/or be easily detectable by an image processing system using data from the optical detector, for example by being highly reflective of infrared radiation (e.g., emitted by an element of tracking system 222). A stereoscopic arrangement of cameras on detection device 246 allows the position of each fiducial to be determined in 3D-space through a triangulation approach. Each fiducial has a geometric relationship to a corresponding object, such that tracking of the fiducials allows for the tracking of the object (e.g., tracking the second fiducial tree 241 allows the tracking system 222 to track the femur 206), and the tracking system 222 may be configured to carry out a registration process to determine or verify this geometric relationship. Unique arrangements of the fiducials in the fiducial trees 240-242 (i.e., the fiducials in the first fiducial tree 240 are arranged in a different geometry than fiducials in the second fiducial tree 241) allows for distinguishing the fiducial trees, and therefore the objects being tracked, from one another.

Using the tracking system 222 of FIG. 2 or some other approach to surgical navigation and tracking, the surgical system 200 can determine the position of the surgical tool 234 relative to a patient's anatomical feature, for example femur 206, as the surgical tool 234 is used to modify the anatomical feature or otherwise facilitate the surgical procedure. Additionally, using the tracking system 222 of FIG. 2 or some other approach to surgical navigation and tracking, the surgical system 200 can determine the relative poses of the tracked bones.

The computing system 224 is configured to create a surgical plan, control the robotic device 220 in accordance with the surgical plan to make one or more bone modifications and/or facilitate implantation of one or more prosthetic components. Accordingly, the computing system 224 is communicably coupled to the tracking system 222 and the robotic device 220 to facilitate electronic communication between the robotic device 220, the tracking system 222, and the computing system 224. Further, the computing system 224 may be connected to a network to receive information related to a patient's medical history or other patient profile information, medical imaging, surgical plans, surgical procedures, and to perform various functions related to performance of surgical procedures, for example by accessing an electronic health records system. Computing system 224 includes processing circuit 260 and input/output device 262.

The input/output device 262 is configured to receive user input and display output as needed for the functions and processes described herein. As shown in FIG. 2, input/output device 262 includes a display 264 and a keyboard 266. The display 264 is configured to display graphical user interfaces generated by the processing circuit 260 that include, for example, information about surgical plans, medical imaging, settings and other options for surgical system 200, status information relating to the tracking system 222 and the robotic device 220, and tracking visualizations based on data supplied by tracking system 222. The keyboard 266 is configured to receive user input to those graphical user interfaces to control one or more functions of the surgical system 200.

The processing circuit 260 includes a processor and memory device. The processor can be implemented as a general purpose processor, an application specific integrated circuit (ASIC), one or more field programmable gate arrays (FPGAs), a group of processing components, or other suitable electronic processing components. The memory device (e.g., memory, memory unit, storage device, etc.) is one or more devices (e.g., RAM, ROM, Flash memory, hard disk storage, etc.) for storing data and/or computer code for completing or facilitating the various processes and functions described in the present application. The memory device may be or include volatile memory or non-volatile memory. The memory device may include database components, object code components, script components, or any other type of information structure for supporting the various activities and information structures described in the present application. According to an exemplary embodiment, the memory device is communicably connected to the processor via the processing circuit 260 and includes computer code for executing (e.g., by the processing circuit 260 and/or processor) one or more processes described herein.

More particularly, processing circuit 260 is configured to facilitate the creation of a preoperative surgical plan prior to the surgical procedure. According to some embodiments, the preoperative surgical plan is developed utilizing a three-dimensional representation of a patient's anatomy, also referred to herein as a "virtual bone model." A "virtual bone model" may include virtual representations of cartilage or other tissue in addition to bone. To obtain the virtual bone model, the processing circuit 260 receives imaging data of the patient's anatomy on which the surgical procedure is to be performed (e.g., femur 206, pelvis 12). The imaging data may be created using any suitable medical imaging technique to image the relevant anatomical feature, including computed tomography (CT), magnetic resonance imaging (MM), and/or ultrasound. The imaging data is then segmented (i.e., the regions in the imaging corresponding to different anatomical features are distinguished) to obtain the virtual bone model. For example, as described in further detail below, MRI-based scan data of a hip can be segmented to distinguish the femur from surrounding ligaments, cartilage, previously-implanted prosthetic components, and other tissue to obtain a three-dimensional model of the imaged hip.

Alternatively, the virtual bone model may be obtained by selecting a three-dimensional model from a database or library of bone models. In one embodiment, the user may use input/output device 262 to select an appropriate model. In another embodiment, the processing circuit 260 may execute stored instructions to select an appropriate model based on images or other information provided about the patient. The selected bone model(s) from the database can then be deformed based on specific patient characteristics, creating a virtual bone model for use in surgical planning and implementation as described herein.

A preoperative surgical plan can then be created based on the virtual bone model. The surgical plan may be automatically generated by the processing circuit 260, input by a user via input/output device 262, or some combination of the two (e.g., the processing circuit 260 limits some features of user-created plans, generates a plan that a user can modify, etc.). In some embodiments, as described in detail below, the surgical plan may be generated and/or modified based on distraction force measurements collected intraoperatively. In some embodiments, the surgical plan may be modified based on qualitative intra-operational assessment of implant fixation (i.e., loose or fixed) and/or intra-operative bone defect mapping after primary implant removal, for example as described in detail below.

The preoperative surgical plan includes the desired cuts, holes, surfaces, burrs, or other modifications to a patient's anatomy to be made using the surgical system 200. For example, for a total knee arthroscopy procedure, the preoperative plan may include the cuts necessary to form, on a femur, a distal surface, a posterior chamfer surface, a posterior surface, an anterior surface, and an anterior chamfer surface in relative orientations and positions suitable to be mated to corresponding surfaces of the prosthetic to be joined to the femur during the surgical procedure, as well as cuts necessary to form, on the tibia, surface(s) suitable to mate to the prosthetic to be joined to the tibia during the surgical procedure. As another example, in a hip arthroplasty procedure, the surgical plan may include the burr necessary to form one or more surfaces on the acetabular region of the pelvis 12 to receive a cup 28(*a*) and, in suitable cases, an implant augment. Accordingly, the processing circuit 260 may receive, access, and/or store a model of the prosthetic to facilitate the generation of surgical plans.

The processing circuit 260 is further configured to generate a control object for the robotic device 220 in accordance with the surgical plan. The control object may take various forms according to the various types of possible robotic devices (e.g., haptic, autonomous, etc). For example, in some embodiments, the control object defines instructions for the robotic device to control the robotic device to move within the control object (i.e., to autonomously make one or more cuts of the surgical plan guided by feedback from the tracking system 222). In some embodiments, the control object includes a visualization of the surgical plan and the robotic device on the display 264 to facilitate surgical navigation and help guide a surgeon to follow the surgical plan (e.g., without active control or force feedback of the robotic device). In embodiments where the robotic device 220 is a haptic device, the control object may be a haptic object as described in the following paragraphs.

In an embodiment where the robotic device 220 is a haptic device, the processing circuit 260 is further configured to generate one or more haptic objects based on the preoperative surgical plan to assist the surgeon during implementation of the surgical plan by enabling constraint of the surgical tool 234 during the surgical procedure. A haptic object may be formed in one, two, or three dimensions. For example, a haptic object can be a line, a plane, or a three-dimensional volume. A haptic object may be curved with curved surfaces and/or have flat surfaces, and can be any shape, for example a funnel shape. Haptic objects can be created to represent a variety of desired outcomes for movement of the surgical tool 234 during the surgical procedure. One or more of the boundaries of a three-dimensional haptic object may represent one or more modifications, such as cuts, to be created on the surface of a bone. A planar haptic object may represent a modification, such as a cut, to be created on the surface of a bone. A curved haptic object may represent a resulting surface of a bone as modified to receive a cup 28a and/or implant augment.

In an embodiment where the robotic device 220 is a haptic device, the processing circuit 260 is further configured to generate a virtual tool representation of the surgical tool 234. The virtual tool includes one or more haptic interaction points (HIPs), which represent and are associated with locations on the physical surgical tool 234. In an embodiment in which the surgical tool 234 is a spherical burr (e.g., as shown in FIG. 2), a HIP may represent the center of the spherical burr. If the surgical tool 234 is an irregular shape, for example as for a sagittal saw, the virtual representation of the sagittal saw may include numerous HIPs. Using multiple HIPs to generate haptic forces (e.g. positive force feedback or resistance to movement) on a surgical tool is described in U.S. application Ser. No. 13/339,369, titled "System and Method for Providing Substantially Stable Haptics," filed Dec. 28, 2011, and hereby incorporated by reference herein in its entirety. In one embodiment of the present invention, a virtual tool representing a sagittal saw includes eleven HIPs. As used herein, references to an "HIP" are deemed to also include references to "one or more HIPs." As described below, relationships between HIPs and haptic objects enable the surgical system 200 to constrain the surgical tool 234.

Prior to performance of the surgical procedure, the patient's anatomy (e.g., femur 206) is registered to the virtual bone model of the patient's anatomy by any known registration technique. One possible registration technique is point-based registration, as described in U.S. Pat. No. 8,010, 180, titled "Haptic Guidance System and Method," granted Aug. 30, 2011, and hereby incorporated by reference herein in its entirety. Alternatively, registration may be accomplished by 2D/3D registration utilizing a hand-held radiographic imaging device, as described in U.S. application Ser. No. 13/562,163, titled "Radiographic Imaging Device," filed Jul. 30, 2012, and hereby incorporated by reference herein in its entirety. Registration also includes registration of the surgical tool 234 to a virtual tool representation of the surgical tool 234, so that the surgical system 200 can determine and monitor the pose of the surgical tool 234 relative to the patient (i.e., to femur 206). Registration of allows for accurate navigation, control, and/or force feedback during the surgical procedure. Additional details relating to registration for hip arthroplasty procedures in some embodiments are described in detail below.

The processing circuit 260 is configured to monitor the virtual positions of the virtual tool representation, the virtual bone model, and the control object (e.g., virtual haptic objects) corresponding to the real-world positions of the patient's bone (e.g., femur 206), the surgical tool 234, and one or more lines, planes, or three-dimensional spaces defined by forces created by robotic device 220. For example, if the patient's anatomy moves during the surgical procedure as tracked by the tracking system 222, the processing circuit 260 correspondingly moves the virtual bone model. The virtual bone model therefore corresponds to, or is associated with, the patient's actual (i.e. physical) anatomy and the position and orientation of that anatomy in real/physical space. Similarly, any haptic objects, control objects, or other planned automated robotic device motions created during surgical planning that are linked to cuts, modifications, etc. to be made to that anatomy also move in correspondence with the patient's anatomy. In some embodiments, the surgical system 200 includes a clamp or brace to substantially immobilize the femur 206 to minimize the need to track and process motion of the femur 206.

For embodiments where the robotic device 220 is a haptic device, the surgical system 200 is configured to constrain the surgical tool 234 based on relationships between HIPs and haptic objects. That is, when the processing circuit 260 uses data supplied by tracking system 222 to detect that a user is manipulating the surgical tool 234 to bring a HIP in virtual contact with a haptic object, the processing circuit 260 generates a control signal to the robotic arm 232 to provide haptic feedback (e.g., a force, a vibration) to the user to communicate a constraint on the movement of the surgical tool 234. In general, the term "constrain," as used herein, is used to describe a tendency to restrict movement. However, the form of constraint imposed on surgical tool 234 depends on the form of the relevant haptic object. A haptic object may be formed in any desirable shape or configuration. As noted above, three exemplary embodiments include a line, plane, or three-dimensional volume. In one embodiment, the surgical tool 234 is constrained because a HIP of surgical tool 234 is restricted to movement along a linear haptic object. In another embodiment, the haptic object is a three-dimensional volume and the surgical tool 234 may be constrained by substantially preventing movement of the HIP outside of the volume enclosed by the walls of the three-dimensional haptic object. In another embodiment, the surgical tool 234 is constrained because a planar haptic object substantially prevents movement of the HIP outside of the plane and outside of the boundaries of the planar haptic object. For example, the processing circuit 260 can establish a planar haptic object corresponding to a planned planar distal cut needed to create a distal surface on the femur 206 in order to confine the surgical tool 234 substantially to the plane needed to carry out the planned distal cut.

For embodiments where the robotic device 220 is an autonomous device, the surgical system 200 is configured to autonomously move and operate the surgical tool 234 in accordance with the control object. For example, the control object may define areas relative to the femur 206 for which a cut should be made. In such a case, one or more motors, actuators, and/or other mechanisms of the robotic arm 232 and the surgical tool 234 are controllable to cause the surgical tool 234 to move and operate as necessary within the control object to make a planned cut, for example using tracking data from the tracking system 222 to allow for closed-loop control.

Figure 3:
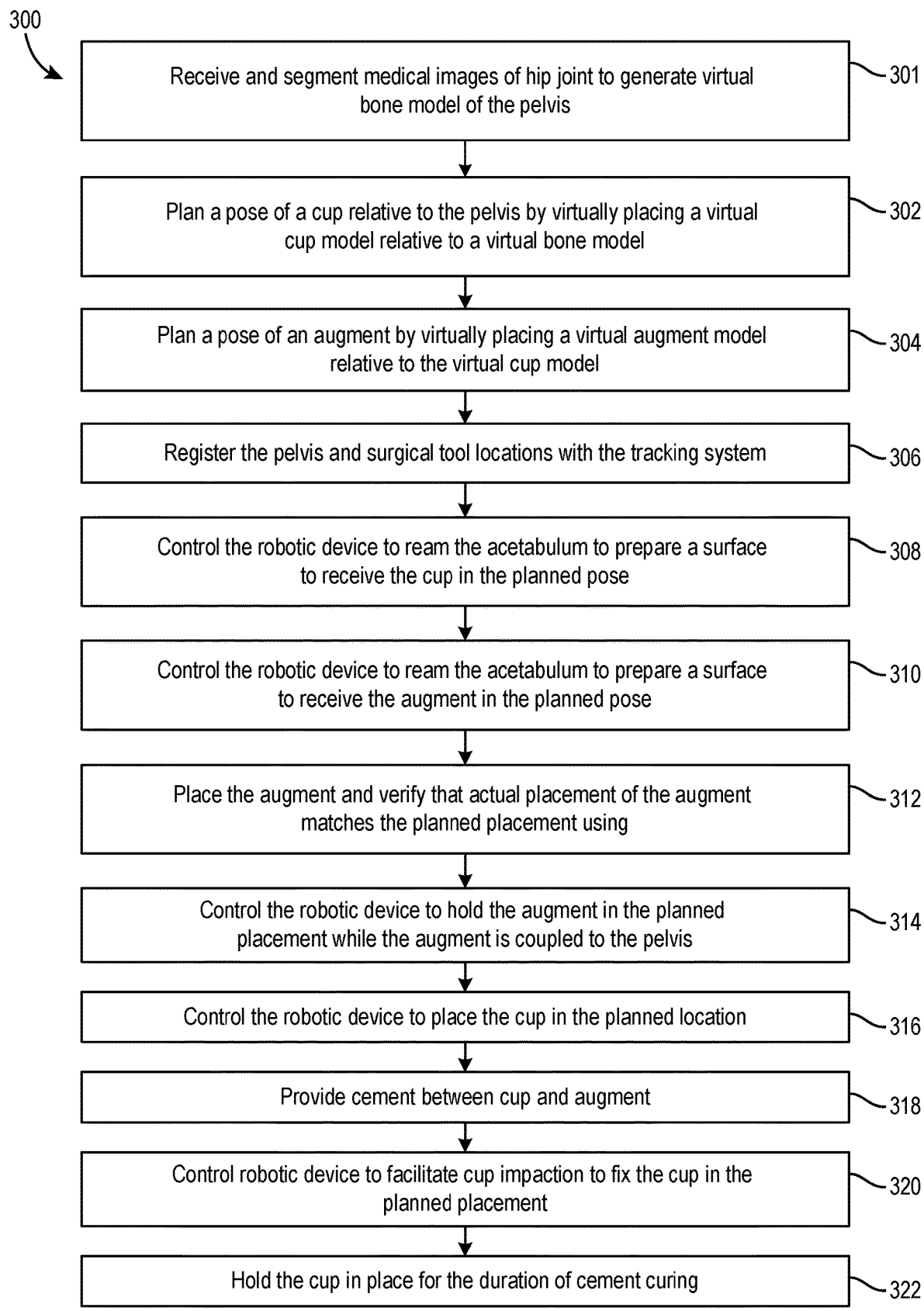
FIG. 3 is a flowchart of a process for facilitating an arthroplasty procedure, according to an exemplary embodiment.

Referring now to FIG. 3, a flowchart of a process 300 for planning and conducting a hip arthroplasty procedure is shown, according to an exemplary embodiment. Process 300 can be executed by the surgical system 200 of FIG. 2. Additionally, FIGS. 4-16 show various systems, methods, graphical user interfaces, etc. used in process 300. Reference is made thereto to facilitate explanation of process 300. It should be understood that process 300 is not limited to the examples of FIGS. 4-16. Additionally, although FIGS. 3-16 illustrate embodiments of process 300 for planning and conducting a procedure relating to a hip, other embodiments are possible for planning and conducting procedures relating to other anatomy, for example shoulders or knees.

At step 301, medical images of the hip joint are received and segmented to generate a virtual bone model of the pelvis. For example, the medical images may be collected using CT technology, MRI technology, or some other medical imaging modality. The images are then segmented, i.e., processed to differentiate areas of the images that correspond to the pelvis, the femur, soft tissue, and/or one or more previously-implanted prosthetic components.

In revision hip arthroplasty cases (i.e., where a previously-implanted cup is shown in the images), a determination may be made of whether the previously-implanted cup is "fixed" (i.e., substantially rigidly coupled to the pelvis) or "loose" (i.e., at least partially detached from the pelvis"). If the previously-implanted cup is fixed, the shape, position, etc. of previously-implanted cup may be determined and included in the virtual bone model of the pelvis, for example to facilitate registration at step 306 as described in detail below. If the previously-implanted cup is loose, the previously-implanted cup may be segmented out such that the loose cup is not included in the virtual bone model of the pelvis. Additionally, various corrections may be introduced to address distortions in CT or other imagery that may be caused by the materials of the previously-implanted cup and/or movement of a loose cup during imaging.

In some embodiments, step 301 is achieved automatically by the processing circuit 260 or other computing resource. In other embodiments, human input is used in cooperation with automated functions to achieve the segmentation and model generation of step 301.

At step 302, placement of an implant cup relative to the pelvis is planned by virtually placing a virtual cup model relative to a virtual bone model, i.e., relative to the virtual model of the pelvis generated at step 301 and, in some cases relative to previously-implanted components (e.g., primary cup, fracture plates, compression screws, etc.). The virtual cup model is a virtual representation of the cup implant to be implanted into the patient during the surgical procedure. Various cup sizes, shapes, types, etc. may be possible, and a different virtual cup model available for each cup. The virtual cup model is placed to provide a desired center of rotation for the hip joint (e.g., relative to the pelvis, relative to a patient's other hip, etc.) and ensure a full range of motion. Various software planning tools may be provided via the surgical system 100 to facilitate a surgeon or other user in selecting and evaluating the pose of the virtual cup model.

Figure 4:
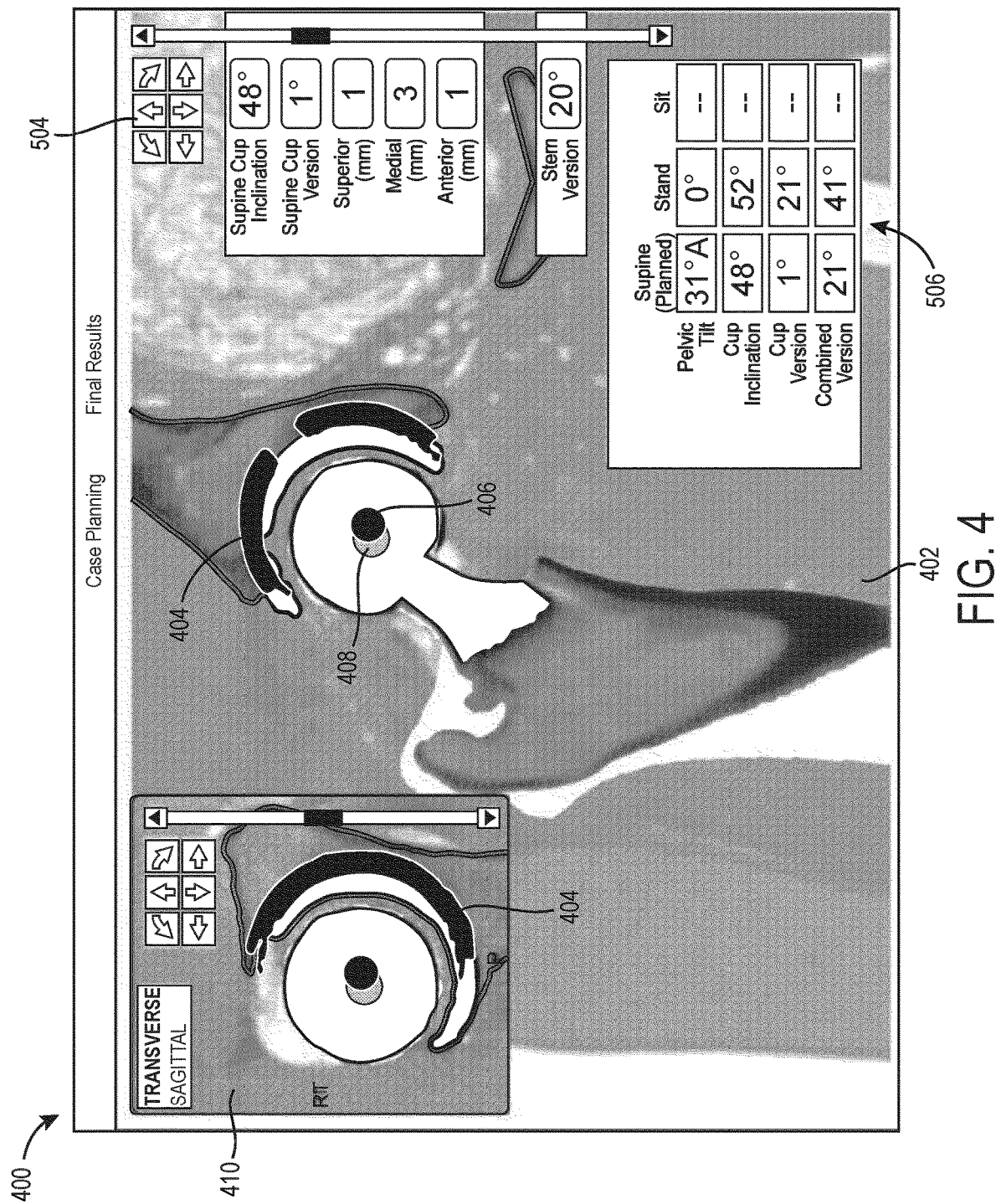
FIG. 4 is a first illustration of a graphical user interface that can be used with the process of FIG. 3, according to an exemplary embodiment.
Figure 5:
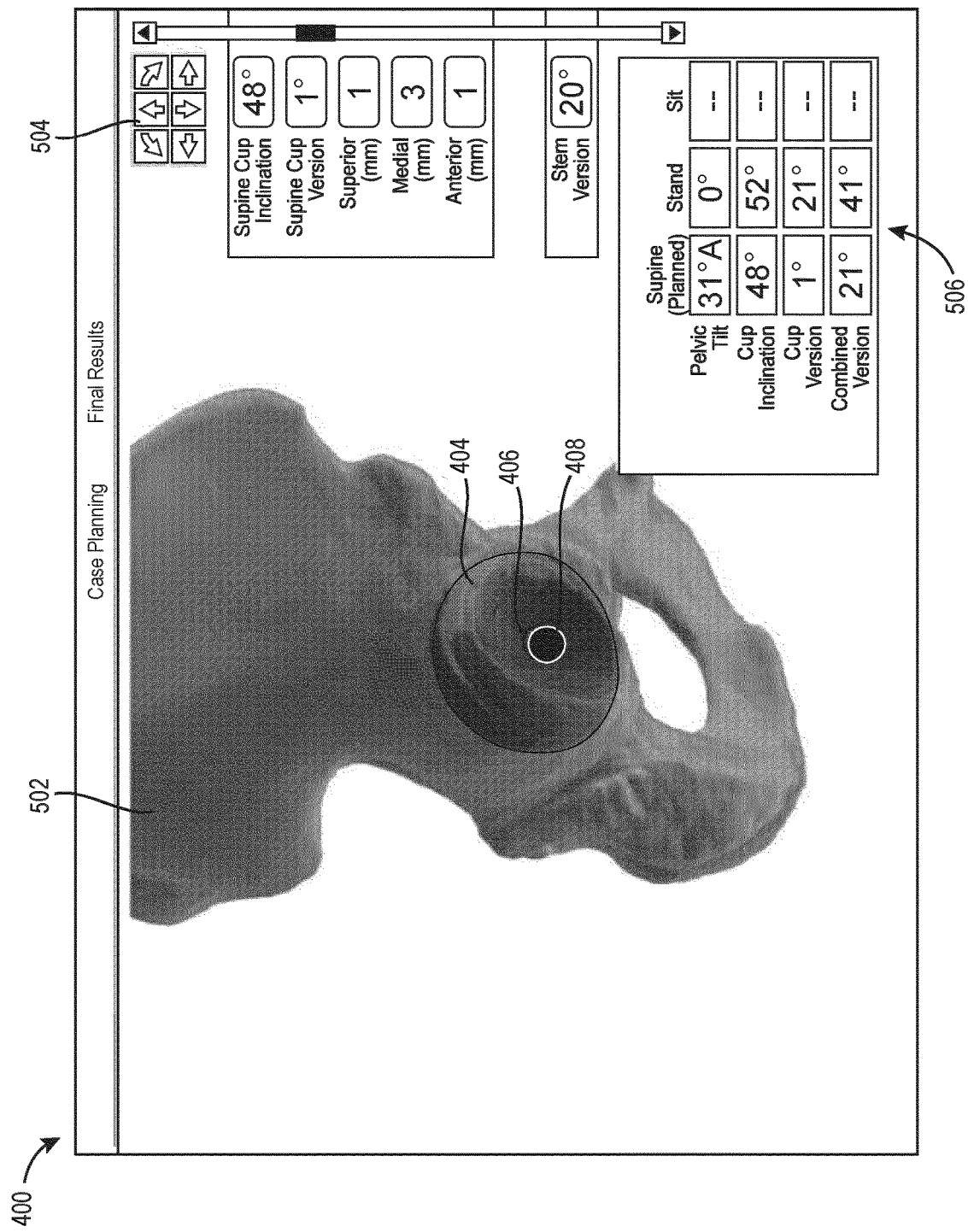
FIG. 5 is a second illustration of a graphical user interface that can be used with the process of FIG. 3, according to an exemplary embodiment.

FIGS. 4-5 illustrate graphical user interfaces that can be generated by the processing circuit 260 and displayed on the display 264 to facilitate planning of cup placement at step 302. FIG. 4 shows a 2-dimensional visualization of a planned cup pose relative to CT images received at step 301. FIG. 5 shows a 3-dimensional visualization of the planned cup pose relative to a virtual bone model generated at step 301. Both are described in further detail below.

In FIG. 4, the graphical user interface 400 includes a first CT image 402 overlaid with a representation of the virtual implant cup 404. A center point (center of rotation) 406 of the virtual implant cup 404 is also shown. Additionally, as shown in FIG. 4, the graphical user interface 400 visualizes the previous center point 408 of the joint as imaged, i.e., before the surgical operation. In the example of FIG. 4, the graphical user interface 400 also shows a second CT image 410 (e.g., taken in a different plane) which is also overlaid with the virtual implant cup 404, the center point 406, and the previous center point 408. Advantageously, bone density information may be visible in the CT images 402, 410. The graphical user interface 400 may thereby facilitate a surgeon in determining placement of the virtual implant cup 404 relative to the imaged bones at step 302.

In FIG. 5, the graphical user interface 400 includes a 3-dimensional visualization of the virtual bone model 502 and of the virtual implant cup 404 placed relative to the virtual bone model 502. The graphical user interface 400 includes a previous center point 408 indicating a center of rotation of the hip joint as determined from the images as well as a center point 406 of the virtual implant cup 404. The graphical user interface 400 thereby facilitates a surgeon in viewing and adjusting the planned pose of the virtual implant cup 404.

As shown in FIGS. 4-5, the graphical user interface 400 includes control arrows 504 that can be selected to translate or rotate the virtual implant cup 404 relative to the virtual bone model 502. The graphical user interface 400 also includes data fields 506 that show various information that may be of interest to the user, for example, pelvic tilt, cup inclination, cup version, stem version, combined version, and superior, medial, and anterior distances. The graphical user interface 400 of FIGS. 4-5 thereby facilitates planning of implant cup placement relative to the pelvis at step 302.

Figure 6:
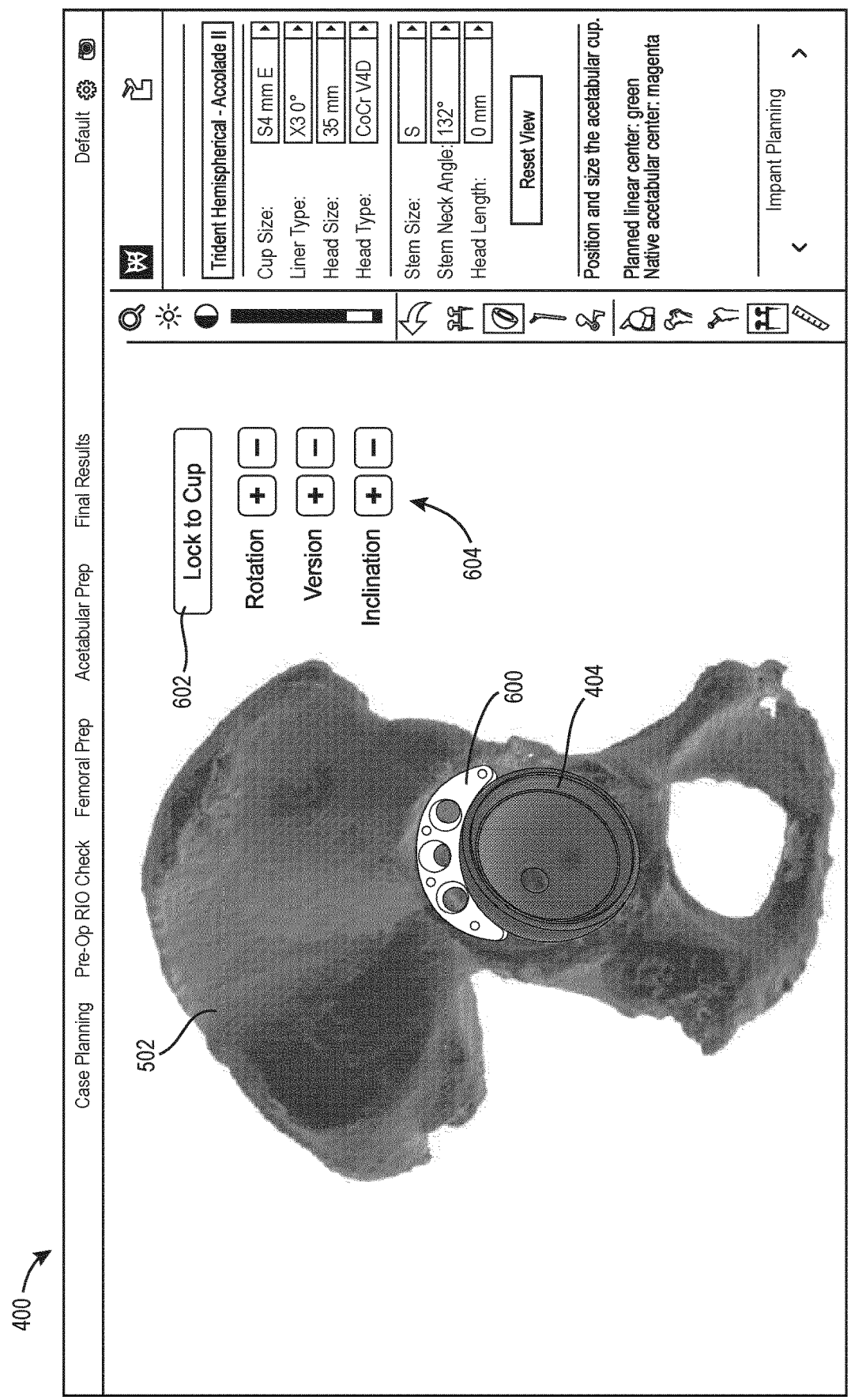
FIG. 6 is a third illustration of a graphical user interface that can be used with the process of FIG. 3, according to an exemplary embodiment.
Figure 7:
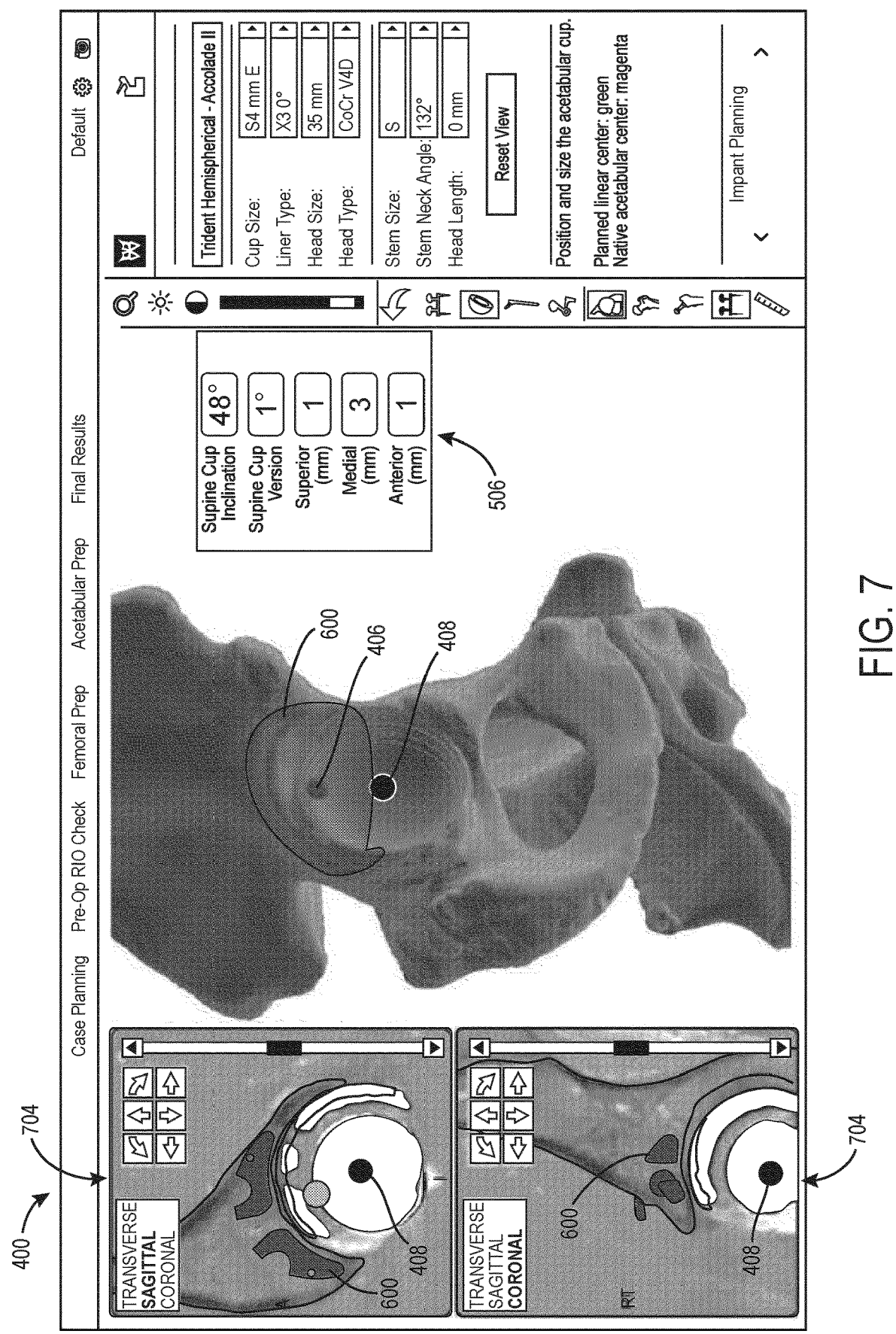
FIG. 7 is a fourth illustration of a graphical user interface that can be used with the process of FIG. 3, according to an exemplary embodiment.

At step 304, placement of an implant augment is planned by virtually placing a virtual augment model relative to the virtual implant cup. For example, a determination may be made based on the visualization of the virtual bone model 502 of FIG. 5 or the CT images of FIG. 4 that an augment may be needed to reliably and securely install the implant cup in the position planed in step 302. An option can be selected via the graphical user interface 400 to include an augment. FIGS. 6-7 show views in the graphical user interface 400 that show a virtual augment model 600 and which facilitate selection of a desired placement of the virtual augment model 600. As shown in FIG. 6, the virtual augment 600 is visualized in a position relative to the virtual bone model 502 and the virtual implant cup 404 in a 3-D opaque view. As shown in FIG. 7, the virtual augment 600 is visualized in a position relative to the virtual bone model 502 in a translucent view and in two CT image views. FIGS. 6-7 are described in further detail below.

In most cases, an implant augment has an interior surface that substantially matches an exterior surface of the implant cup, for example having a degree of curvature or radius substantially equal to the exterior surface of the implant cup. The augment is thereby configured to be placed adjacent to the implant cup and to provide structural support for the implant cup.

As shown in FIG. 6, the graphical user interface 400 includes a lock-to-cup button 602. When the lock-to-cup button 602 is selected, the virtual augment 600 is restricted to a pre-defined spacing relative to virtual cup 404. For example, the virtual augment 600 may be positioned such that the virtual augment 600 is approximately two millimeters from the virtual cup 404. This spacing provides a volume which may be filled with cement or other adhesive during the procedure to couple the augment to the cup. As shown in FIG. 6, the graphical user interface 400 includes an array of control buttons 604 that can be selected to alter the rotation, version, and inclination of the virtual augment 600 while preserving the pre-defined spacing relative to the virtual cup 404. Accordingly, step 304 may include restricting the planned placement of the implant augment to a pre-defined spacing relative to the planned position of the cup.

As shown in FIG. 7, the graphical user interface 400 shows a representation of the virtual augment 600 and the virtual bone model 502 without the virtual cup 404. As shown in FIG. 7, the graphical user interface 400 may facilitate a surgeon in evaluating the contribution of the virtual augment 600 to formation of a surface for receiving the cup. CT views 704 show two-dimensional views of the virtual augment 600 relative to CT images collected of the patient's hip. The CT images may show bone density, a previously-implant cup, other implant components (e.g., screws, plates, etc. used to treat traumatic injury), and/or other useful information. The graphical user interface 400 of FIGS. 6-7 thereby facilitate planning of the implant augment relative to the implant cup and the pelvis. The graphical user interface 400 may also facilitate planning of screw trajectories of the implant and the augment, so that such screw trajectories are considered/planned simultaneously. This may ensure that the augment and implant cup are positioned such that the screws will not interfere with one another or with any existing hardware (e.g., trauma screws/plates). The screw trajectories may also be visualized relative to bone density to ensure adequate screw fixation is achieved.

Steps 302 and 304 can thereby result in a planned pose of the implant cup and a planned pose of the implant cup. Such planning (i.e., steps 301-304) may occur pre-operatively and/or intraoperatively. The remaining steps of process 300 occur intraoperatively, i.e., during the surgical procedure.

At step 306, a registration process is executed to register the relative positions of the patient's pelvis, the surgical tool(s), the robotic device, and/or other tracked probes or instruments. For example, a probe may be tracked by the tracking system 222 and touched to various points on the pelvis to determine a pose of the pelvis. Various registration methods are described above with reference to FIG. 2.

Figure 8:
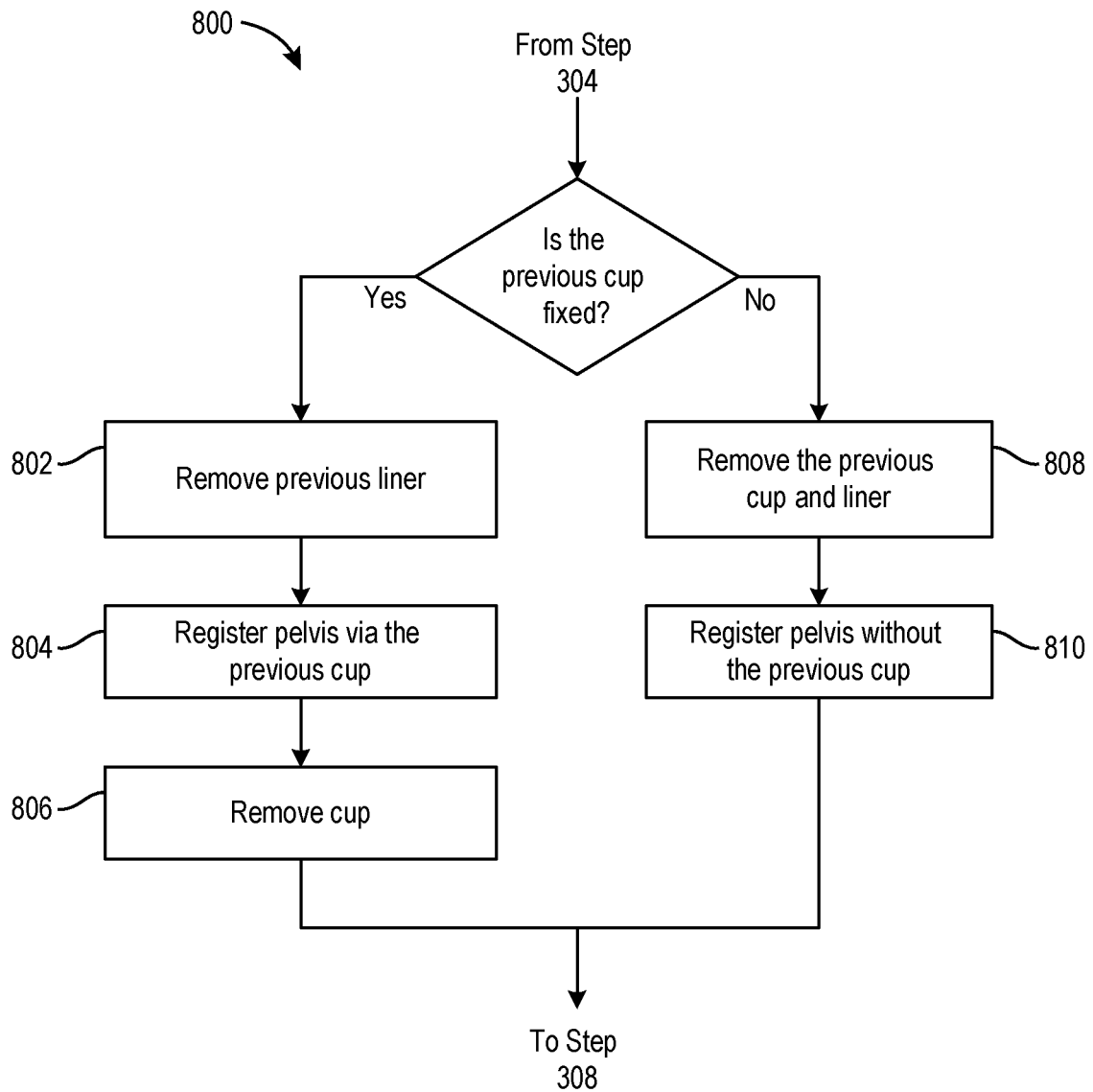
FIG. 8 is a flowchart of showing a detailed view of steps of the process of FIG. 3, according to an exemplary embodiment.

In the case of revision hip arthroplasty procedures, different registration workflows may be used depending on whether the previously-implanted cup is loose or fixed. FIG. 8 shows a flowchart of a process 800 for registration in revision hip arthroplasty procedures, according to an exemplary embodiment.

As illustrated in FIG. 8, if the previous cup is fixed, the liner of the previous implant (i.e., implanted in a previous procedure) is removed at step 802. At step 804, the location of the pelvis is registered via the previous implant cup, which is fixed to the pelvis. For example, a tracked probe can be touched to various locations on the previous implant cup to determine a pose of a surface of the previous implant cup. As another example, intra-operative imaging (e.g., x-ray) may be used to determine a pose of a surface of the previous implant cup. Because the geometric relationship between the previous implant cup and the pelvis is fixed and known from the medical images received at step 301, such data can be used for registration of the pelvis. A tracked probe and/or intraoperative imaging may also be used to locate and register existing hardware (e.g., trauma screws/plates) to facilitate avoidance of such structures during a procedure (e.g., by creating virtual control objects around the located positions of such structures). Following registration, the previous cup is removed at step 806 to allow the revision implant to be installed. In some embodiments, haptic guidance is used to facilitate removal the previous (primary, existing) implant, for example as described in U.S. Patent Application 20180014891. For example, a virtual control object can be generated by referencing a library of implant designs to determine a geometry of the relevant implant, identifying the edges of the previous implant using a probe, and generating haptic boundaries based on the probed edges.

Also as illustrated in FIG. 8, the previous cup is loose (i.e., not fixed), the previous cup and liner are removed at step 808 prior to registration of the pelvis. At step 810, the pelvis is registered without the previous cup. For example, a probe may be touched to various points around or in the region from which the previous cup was removed.

Figure 10:
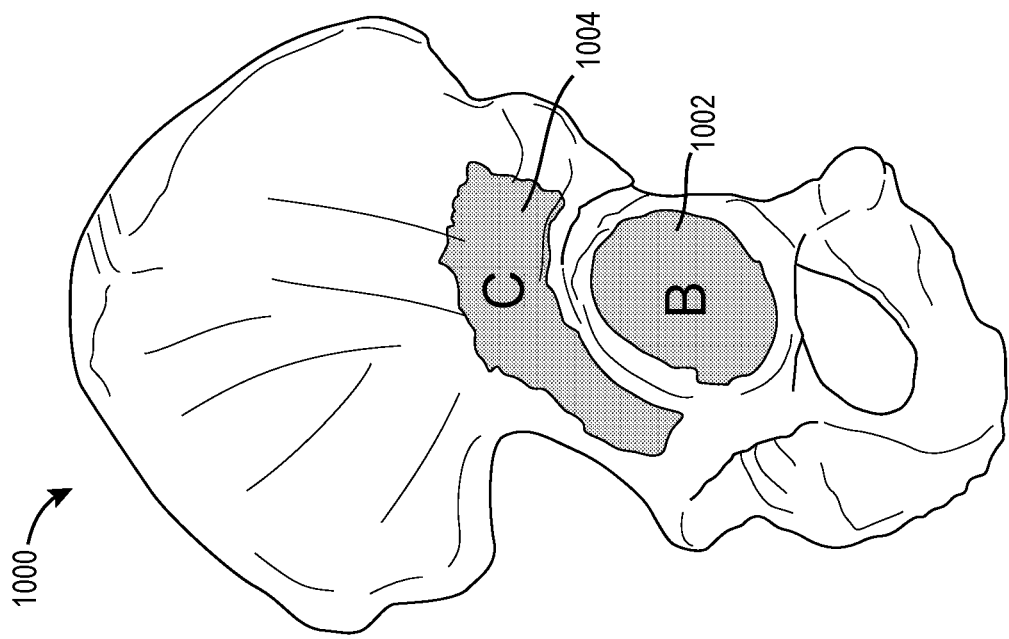
FIG. 10 is a second visualization of registration regions on a pelvis for use with the process of FIG. 3, according to an exemplary embodiment.
Figure 9:
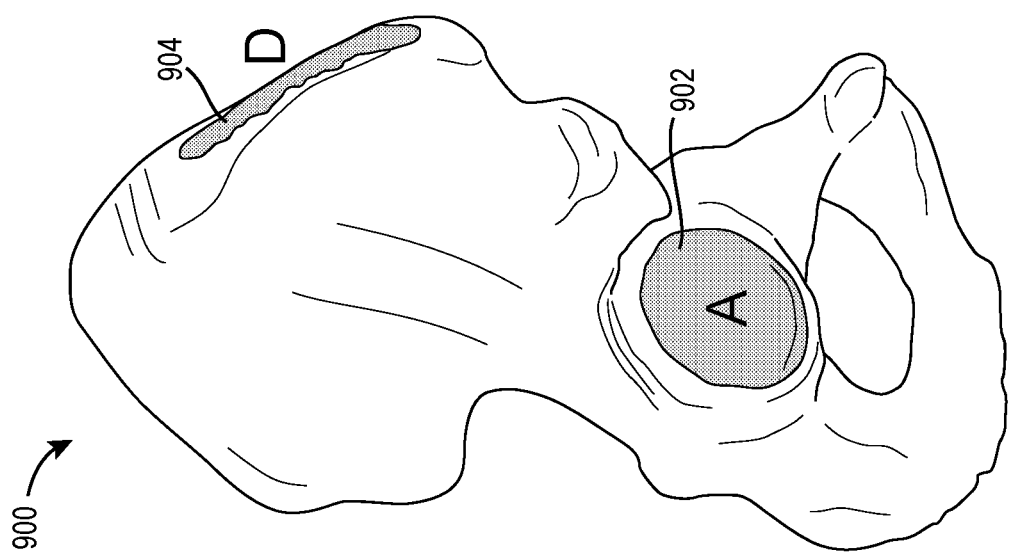
FIG. 9 is a first visualization of registration regions on a pelvis for use with the process of FIG. 3, according to an exemplary embodiment.

To further illustrate the registration of step 306 according to some embodiments, FIGS. 9-10 depict regions of the pelvis that may be used for registration in various scenarios. FIG. 9 illustrates a virtual bone model 900 that includes a fixed cup, while FIG. 10 illustrates a virtual bone model 1000 in which a loose cup has been removed, leaving an approximated, smooth surface. FIGS. 9-10 including demarcation of several registration regions, shown as region A 902, region B 1002, region C 1004, and region D 904.

In a scenario with a fixed cup, registration points (i.e., points touched by a tracked probe and used for registration) can be taken in region A 902, which corresponds to a surface of the previously-implanted fixed cup. Such points may be particularly reliable and accessible, as region A 902 is exposed during surgery to allow for removal of the previously-implanted cup. Other points may also be taken, for example in region D 904 (along the iliac crest) and/or region C 904 (above the acetabulum).

In a scenario with a loose cup, registration points can be taken in region B 1002, which corresponds to an acetabular surface exposed when the loose cup is removed from the patient. For example, registration points may be taken around a rim of region B 1002. The reliability of such points may be dependent on the accuracy of the segmentation of step 301 in differentiating the surface of the bone in the pre-operative imagery from the loose cup, which is removed to expose the surface of region B 1002. In some embodiments, registration of the pelvis is achieved in the loose cup scenario without using acetabular registration points (without using registration points in region A 902 or region B 904) and by using extra-acetabular registration points (e.g., points in region C 1004 and/or region D 904).

Registration as conducted at step 306 thereby facilitates a mapping of the actual pose of the pelvis in real space to a virtual position of the virtual bone model 502 in virtual space. The virtually-planned poses of the virtual implant augment and the virtual implant cup can then also be associated with real poses in real space (e.g., relative to a coordinate system used by the tracking system 222).

The primary cup (i.e., the existing implant) can then be removed using standard techniques. In some cases, removal of the primary cup may result in an unexpected defect cavity which was not accounted for the original surgical plan. In such cases, the tracked probe may be used to define a contour (size, shape, pose, etc.) of the defect cavity, for example by tracking the location of the probe as the probe is touched to various positions on the surface of the defect cavity, traced/painted along the defect cavity, etc. The virtual bone model may then be updated to include a virtual representation of the defect cavity, so that the virtual bone model substantially matches the actual form of the bone after primary cup removal. The surgical plan can then be adjusted to account for the defect cavity, for example by modifying a size or pose of an augment. Intra-operative registration and bone model updates can also be used to correct for voids from a segmentation process or clarify regions of scatter in the original imaging (e.g., CT images).

Similar updates may be made in response to identification other features that may be located and registered intra-operatively, for example poor bone stock, cysts, etc. In some embodiments, custom virtual control boundaries are automatically generated intra-operatively based on the tracked positions of a probe moved by a user to positions indicating the location of a feature desired to be resected (e.g., a cyst). The robotic device 220 can then be controlled based on the custom virtual control boundary to resect the identified feature.

Additionally, in some embodiments, the virtual bone model may be updated following an initial resection (e.g., osteophyte resection). For example, a cutting accessory (e.g., attached to the robotic device 220) may be tracked relative to the bone as the cutting accessory is used to remove an osteophyte or other feature. Based on the tracked movement of the cutting accessory, the virtual bone model can be automatically updated to include the modifications made by the cutting accessory by removing the portions of the virtual bone model corresponding to the resected features. The virtual bone model can thereby be updated to accurately represent the post-resection bone surface without reimaging. The surgical plan for remaining steps of the procedure can be updated based on the updated virtual bone model, or other interventions can be planed (e.g., bone graft to fill a void, etc.).

At step 308, the robotic device 220 is controlled to ream the acetabulum to prepare a surface of the pelvis to receive the cup in the planned pose. For example, a virtual control object may be generated based on the planned pose of the cup (referred to herein as the "cup virtual control object"). For example, the cup virtual control object may include a surface corresponding to an exterior surface of the cup and arranged in the planned pose of the cup. Such a surface of the cup virtual control object defines a planned bone modification, e.g., a resulting configuration of the bone after a machining (e.g., reaming) process such that the bone is prepared to receive the cup implant in the planned pose.

The robotic device 220 may be controlled at step 308 using the cup virtual control object. In some embodiments, the robotic device 220 executes autonomous movements as guided by the cup virtual control object to move and operate the surgical tool 234 to ream the pelvis to prepare the pelvis to receive the cup in the planned position. In other embodiments, the robotic device 220 provides haptic feedback to a user to constrain the surgical tool 234 within the cup virtual control object as a user manipulates the surgical tool 234 to ream the pelvis to prepare the pelvis to receive the cup in the planned position. These and other possible control modalities are described in detail above with reference to FIG. 2.

Figure 11:
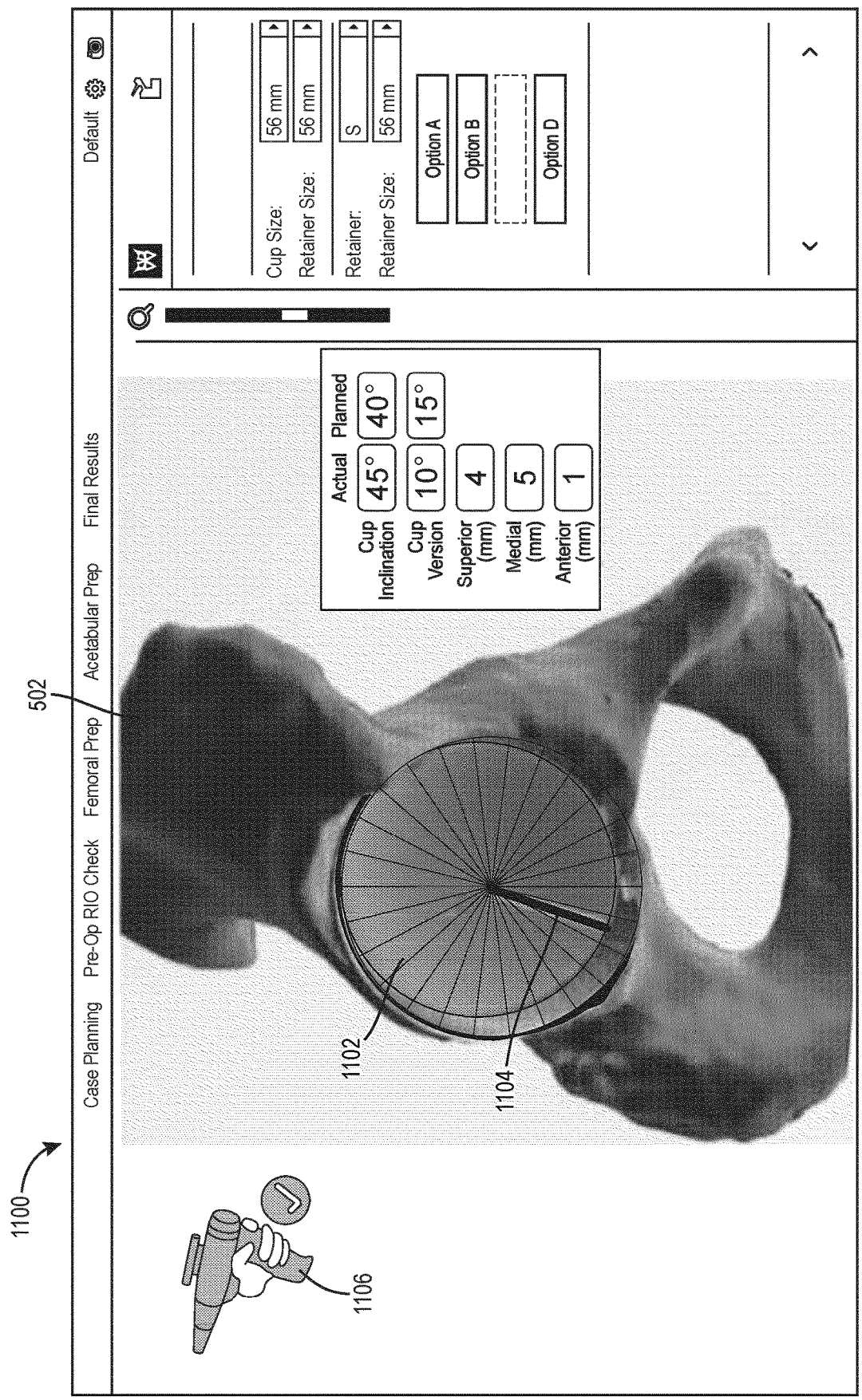
FIG. 11 is a fifth illustration of a graphical user interface that can be used with the process of FIG. 3, according to an exemplary embodiment.

FIG. 11 shows an example of a graphical user interface 1100 that may be generated by the processing circuit 260 and displayed on the display 264 to facilitate execution of step 308, for example an in embodiment where the robotic device 220 is a haptic device. The graphical user interface 1100 shows the virtual bone model 502 with a color-coded (e.g., green) or shaded region 1102 indicating areas of the bone that are to be removed in accordance with the surgical plan. An arrow 1104 indicates a current orientation and center point of the surgical tool 234. A tool indicator 1106 indicates that the surgical tool 234 is currently operating (e.g., that the reamer is rotating).

The processing circuit 260 is configured to update the graphical user interface 1100 in real time using the tracked poses of the pelvis and the surgical tool 234 from the tracking system 222. For example, the color-coded or shaded region 1102 may be reduced in size as the tracking data indicates that the cutting accessory of the surgical tool 234 (e.g., the head of a reamer tool) passes through the corresponding area of the bone. Completion of the planned bone modification corresponds to full consumption (reduction to nothing, erasure, etc.) of the color-coded or shaded region 1102.

The virtual control object may also be indicated on the graphical user interface 1100. In some cases, the processing circuit 260 may provide a different color-coding (e.g., red) to indicate areas where data from the tracking system 222 indicates that surgical tool 234 violated the constraints of the virtual control object and modified the bone beyond the surgical plan.

At step 310, the robotic device 220 is controlled to ream the acetabulum to prepare a surface of the pelvis to receive the implant augment in the planned pose of the implant augment.

For example, a virtual control object may be generated based on the planned pose of the augment (referred to herein as the "augment virtual control object"). For example, the augment virtual control object may include a surface corresponding to an exterior surface of the augment and arranged in the planned pose of the augment. Such a surface of the augment virtual control object defines a planned bone modification, e.g., a resulting configuration of the bone after a machining process such that the bone is prepared to receive the augment implant in the planned pose.

In some embodiments, the cup virtual control object and the augment virtual control object are separate virtual control objects and are applied sequentially to execute the surgical plan by first preparing the bone to receive the cup and then preparing the bone to receive the augment. In some cases, the sequence may be reversed, such that the robotic device 220 is controlled to first prepare the bone to receive the augment using the augment virtual control object and then the cup virtual control object is applied to control the robotic device 220 to prepare the bone to receive the cup.

In some such embodiments, a different approach orientation for the surgical tool may be required by the cup virtual control object and the augment virtual control object. The processing circuit 260 may determine completion of the first bone modification (i.e., an end of step 308) and guide the surgical tool from the orientation required by the cup virtual control object into the orientation required by the augment virtual control object, for example using a collapsing haptic boundary, before initiating the second bone modification (i.e., execution of step 310). Additionally, in some embodiments, a change to the surgical tool 234 may be made between steps 308 and 310, for example such that a first reamer head with a first size is used to prepare the cup region and a second reamer head with a second (e.g., smaller) size is used to prepare the bone to receive the augment. The graphical user interface 1100 may display a prompt to make such a change to the surgical tool 234.

In other embodiments, the cup virtual control object and the augment virtual control object are combined as a single virtual control object that includes surfaces corresponding to both the cup and the augment. In such embodiments, steps 308 and 310 can be executed in a unified (simultaneous) manner.

Figure 12:
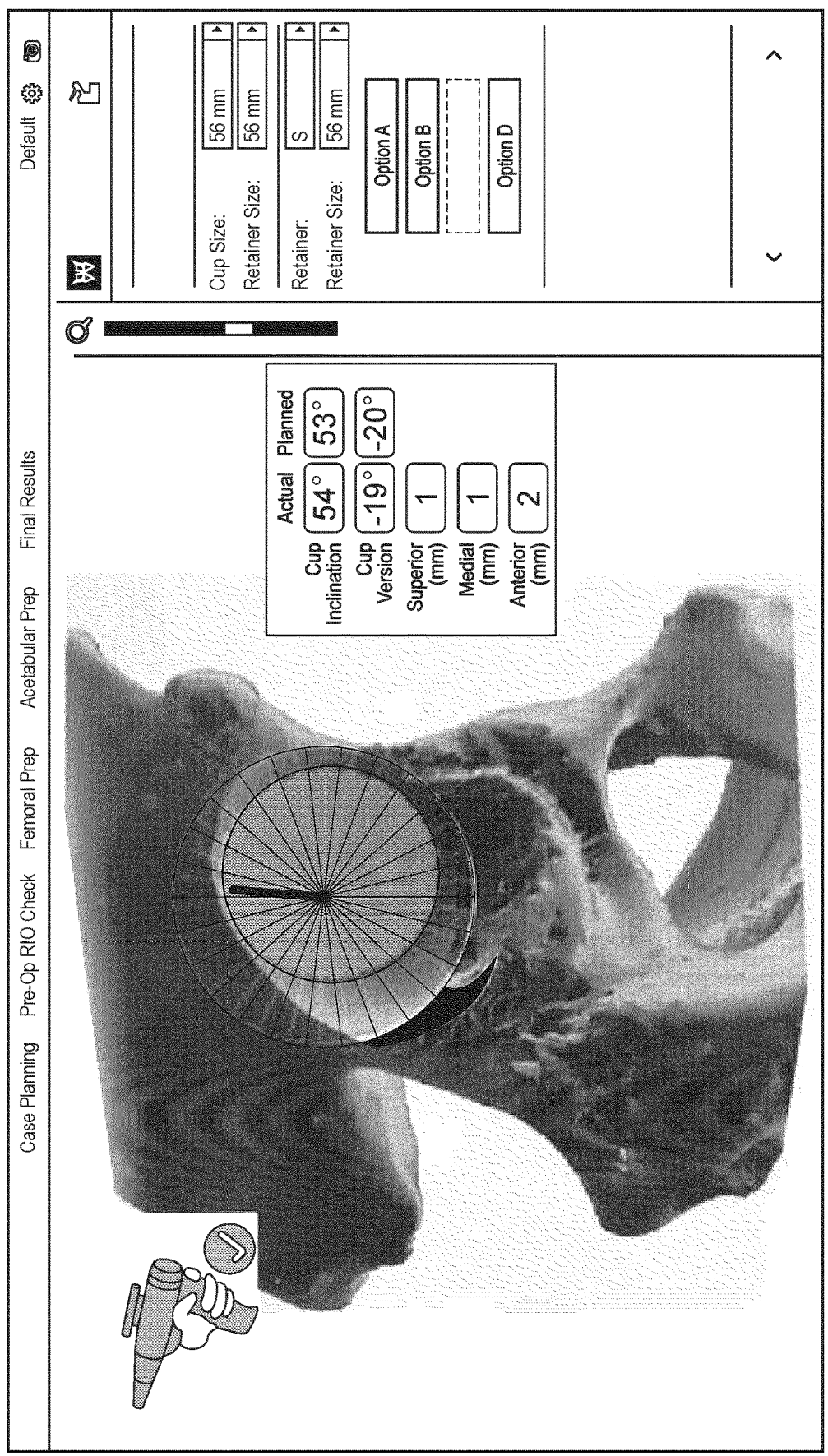
FIG. 12 is a sixth illustration of a graphical user interface that can be used with the process of FIG. 3, according to an exemplary embodiment.

FIG. 12 shows the graphical user interface 1100 as displayed during step 310 in an exemplary embodiment. The graphical user interface 1100 shows the virtual bone model 502 with a color-coded (e.g., green) or shaded region 1102 indicating areas of the bone that are to be removed in accordance with the surgical plan during step 310. The virtual bone model 502 has been modified by the processing circuit 260 to visualize the modifications to the actual bone made during step 308. An arrow 1104 indicates a current orientation and center point of the surgical tool 234. In the example shown, the arrow 1104 has changed orientation relative to the orientation of the arrow 1104 as shown in FIG. 11. A tool indicator 1106 indicates that the surgical tool 234 is currently operating (e.g., that the reamer is rotating).

To facilitate step 308, the processing circuit 260 is configured to update the graphical user interface 1100 in real time using the tracked poses of the pelvis and the surgical tool 234 from the tracking system 222. For example, the color-coded or shaded region 1102 may be reduced in size as the tracking data indicates that the cutting accessory of the surgical tool 234 (e.g., the head of a reamer tool) passes through the corresponding area of the bone. Completion of the planned bone modification corresponds to full consumption (reduction to nothing, erasure, etc.) of the color-coded or shaded region 1102.

Steps 308 and 310 thereby result in a bone (e.g., pelvis) prepared to receive the cup in the pose planned at step 302 and to receive the implant in the pose planned at step 304.

Figure 13:
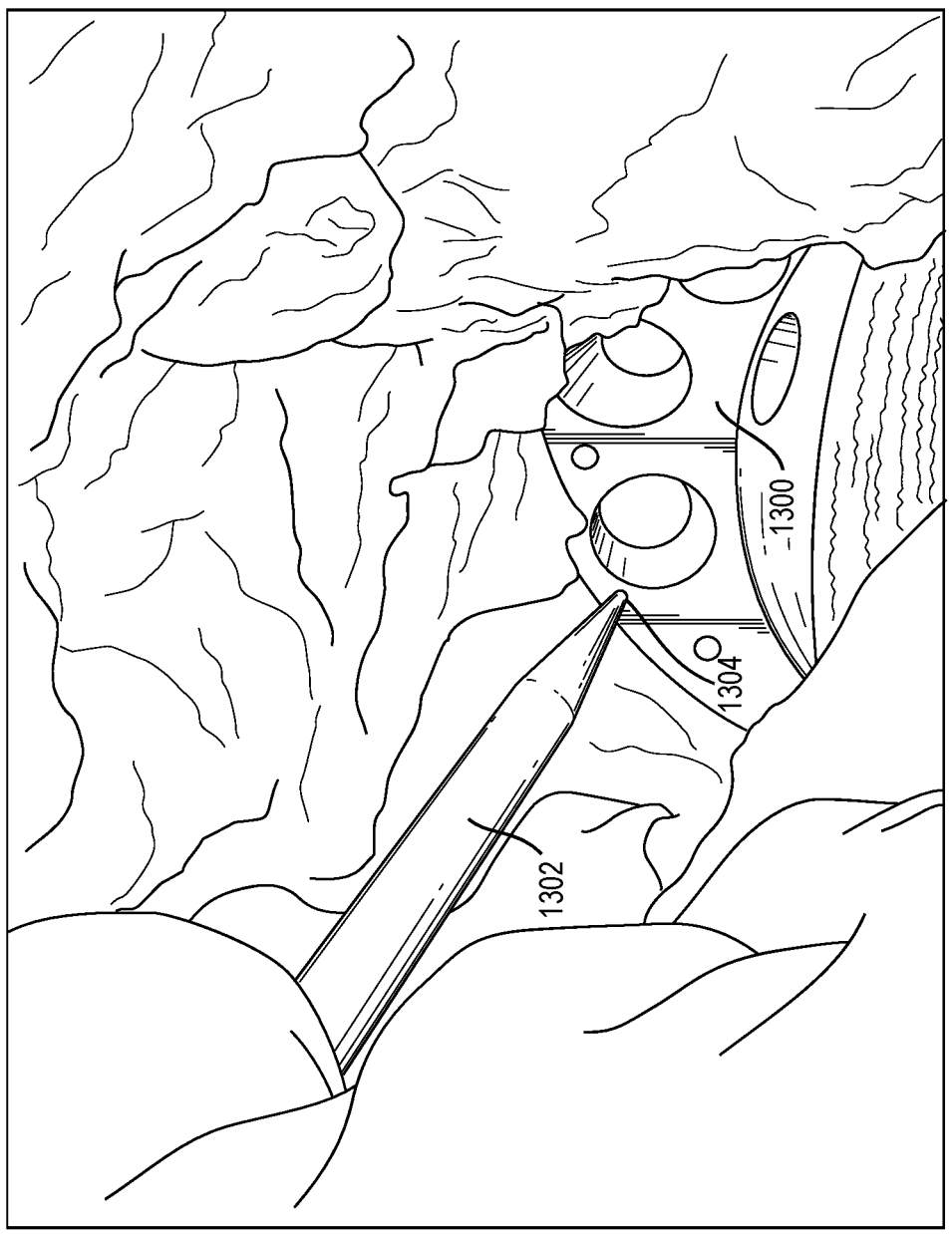
FIG. 13 is a depiction of an implant augment and a probe as used in the process of FIG. 3, according to an exemplary embodiment.

At step 312, the augment is placed in the planned pose and a match between the actual pose of the augment and the planned pose is verified, for example as illustrated in the example embodiment of FIG. 13. As shown in FIG. 13, a surgeon has manually placed the augment 1300 in the surgical site and adjacent the bone in approximately the planned pose. A navigation probe 1302 is shown as touching a point on the augment 1300. The navigation probe 1302 can be tracked by the tracking system 222, such that the tracking system 222 can ascertain a location of the tip 1304 of the probe 1302 relative to other tracked objects, for example the bone modified at steps 308-310. By tracking the navigation probe 1302 as the navigation probe 1302 is touched to multiple points on the augment 1300, a pose of the augment 1300 can be determined by the tracking system 222 and the processing circuit 260. In such embodiments, the processing circuit 260 is configured to compare the tracked pose of the augment 1300 to the planned pose of the augment from step 304. The processing circuit 260 may cause the display 264 to display an indication that the tracked pose of the augment 1300 matches the planned pose of the augment and/or provide guidance for modifying the actual pose of the augment 1300 to bring the tracked pose of the augment 1300 into agreement with the planned pose of the augment 1300. In other embodiments, the augment 1300 may be coupled to a tracked inserter tool, such that the processing circuit can use the tracked pose of the inserter tool to facilitate navigation of the augment to the planned pose. In some embodiments, the inserter tool is supported by the robotic device 220 or another robotic arm such that the inserter tool can hold the augment 1300 in a selected position.

Figure 14:
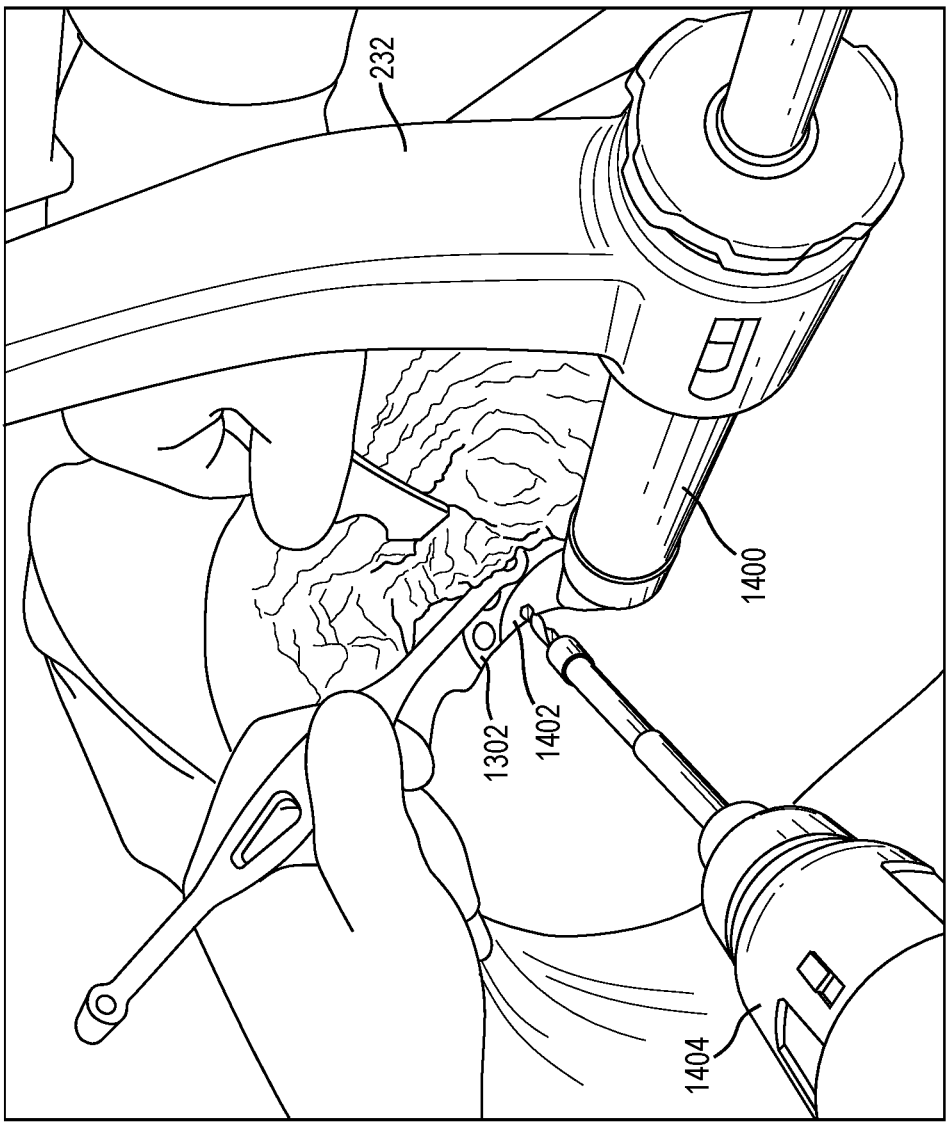
FIG. 14 is a depiction of fixation of the implant augment of FIG. 13 to a bone as in the process of FIG. 3, according to an exemplary embodiment.

At step 314, the robotic device 220 is controlled to hold the augment in the planned placement while the augment is coupled to the pelvis, for example as illustrated in the example embodiment of FIG. 14. As shown in FIG. 14, the augment 1300 is positioned as described with reference to FIG. 13 and step 312. A holder arm 1400 is coupled to the robotic arm 232 and is shown as holding a trial cup implant 1402. The robotic arm 232 is controlled to force the trial cup implant 1402 against the augment 1300 to push the augment 1300 against the bone, thereby holding the augment 1300 in the planned pose relative to the bone. The augment 1300 can then be coupled to the bone. In the example of FIG. 14, a surgical drill 1404 (e.g., a flexible drill) is used to insert one or more screws through the augment 1300 and into the bone to secure the augment 1300 to the bone in the planned position. The trial cup implant 1402, as held in position by the robotic device 220, can substantially prevent movement of the augment 1300 while the screws are inserted, thereby reducing the number of surgeons or surgical assistants needed to conduct the surgery, improving visibility of the surgical field, and improving accuracy of placement of the augment 1300 relative to the surgical plan. Although a trial cup implant is used in this embodiment, a final cup implant may also be used in step 314.

In other embodiments, at step 314, the augment 1300 is coupled to the holder arm such that the holder arm can be moved by the robotic device 220 to adjust the position of the augment 1300. In such an embodiment, the robotic device 220 is controlled to move the augment 1300 to the planned pose, for example autonomously or by providing haptic feedback to a surgeon. In some embodiments, the surgical drill 1404 is robotically-controlled (e.g., coupled to a second robotic arm) and configured to autonomously insert screws through the augment into the bone in accordance with a surgical plan. In some embodiments, a cutting accessory of surgical tool 234 can be used (autonomously or under haptic guidance) to prepare pilot holes for screw insertion. In some such embodiments, a screw insertion accessory can then be mounted to surgical tool 234 to insert (autonomously or under haptic guidance) bone screws into the pilot holes and through the augment.

At step 316, the implant cup is placed in substantially the planned pose for the implant cup (e.g., slightly spaced from the planned pose in anticipation of step 320 described below). In some embodiments, the cup is manually positioned by a surgeon and that position is checked using a navigation probe as described above for the augment with reference to step 312. In other embodiments, the implant cup is mounted on an impaction arm coupled to the robotic device 220. The robotic device 220 is controlled to move the implant cup to substantially the planned pose, for example autonomously or by providing haptic feedback to a user. For example, haptic feedback may be provided by constraining the position of the implant cup within a virtual control object that collapses (gets smaller, converges) as the implant cup is brought closer to the planned pose, i.e., such that the implant cup can be moved closer to the planned pose but not substantially further away from the planned position relative to a current position. The implant cup is thereby positioned and oriented in substantially the planned pose.

At step 318, cement is provided between the cup and the augment. As mentioned above with reference to step 304, the planned pose of the augment is spaced apart from the planned pose of the cup to allow for cement to be included between the cup and the augment to couple the cup to the augment. By following steps 312-316, the actual positions of the cup and the augment also provide space for cement between the cup and the augment. Accordingly, process 300 facilitates use of a predictable, consistent, and preferred (planned, clinically-validated, etc.) amount of cement between the cup and the augment.

Figure 15:
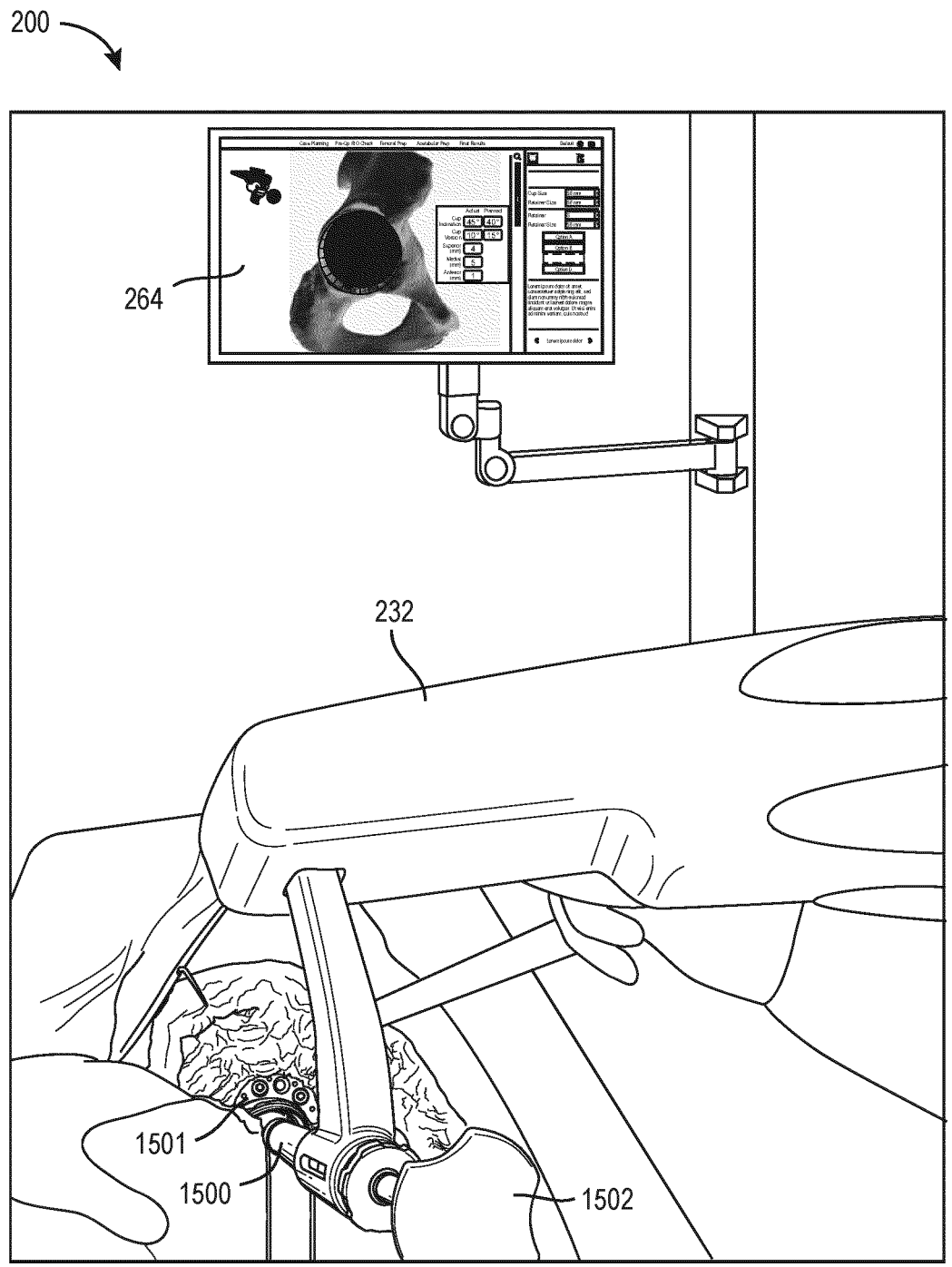
FIG. 15 is a depiction of a cup impaction step of the process of FIG. 3, according to an exemplary embodiment.

At step 320, the robotic device is controlled to facilitate cup impaction to fix the cup in the planned placement. FIG. 15 shows an example embodiment of the surgical system 200 arranged to execute step 320. As shown in FIG. 15, an impaction device 1500 is mounted on the robotic arm 232. The robotic arm 232 is controlled to align the impaction device 1500 with the planned orientation of the cup and such that a distal end 1501 of the impaction device 1500 is in contact with the cup at substantially the planned position for the cup. FIG. 15 shows the display device 264 as providing an indication that the impaction device 1500 is properly positioned for cup impaction. When the surgical system 200 is in the state shown in FIG. 15, the surgeon may provide a blunt force to a proximal end 1502 of the impaction device 1500. The force is transmitted along the impaction device 1500 to impact the cup into the pelvis. This force causes the cup to be driven into the pelvis to substantially fix the cup relative to the pelvis. The robotic arm 232 and information displayed on the display device 264 facilitates a surgeon in accomplishing impaction such that the cup is fixed to the pelvis in the planned pose (i.e., as planned at step 302).

Figure 16:
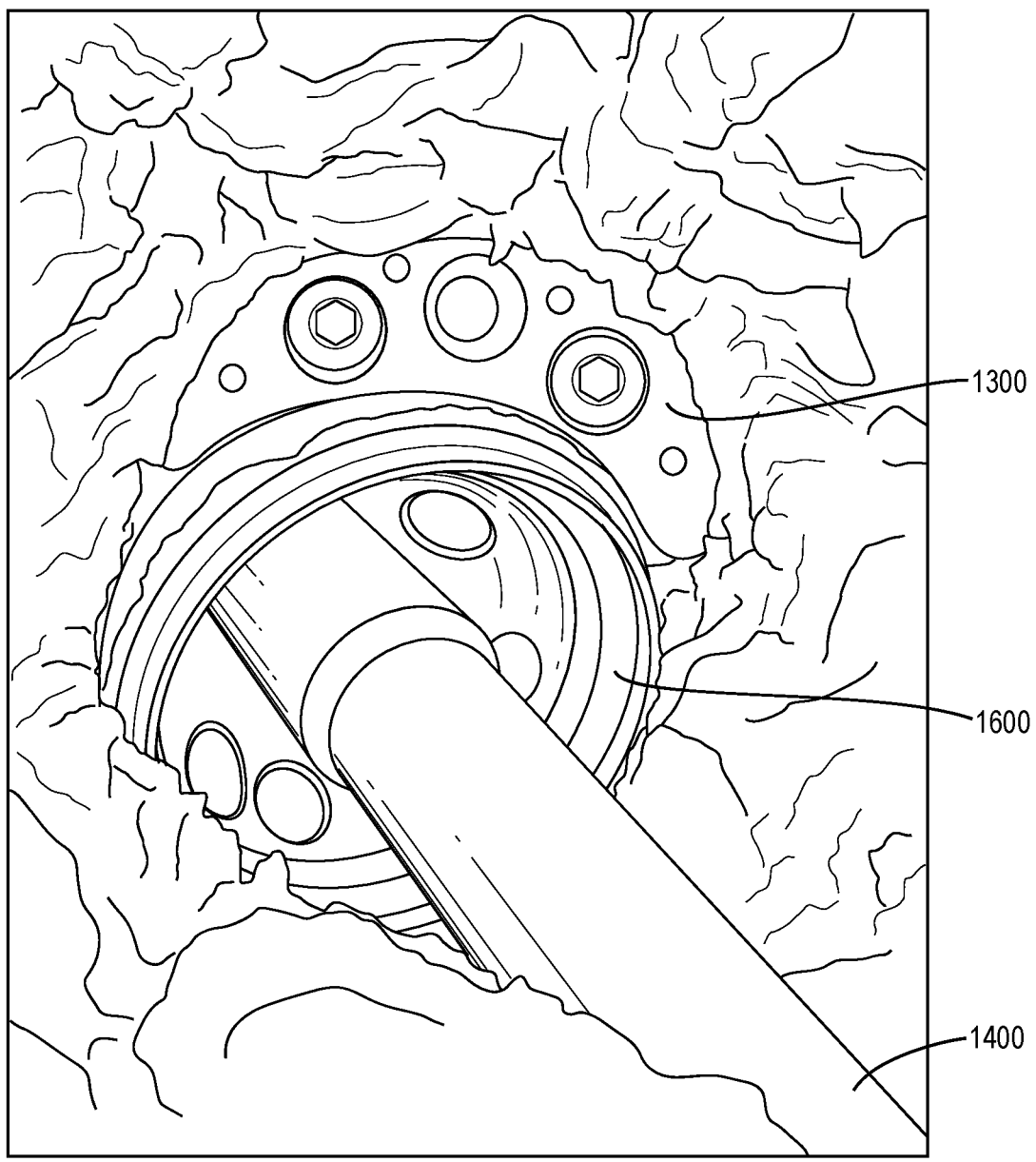
FIG. 16 is a depiction of a cement curing step of the process of FIG. 3, according to an exemplary embodiment.

At step 322, the robotic device is controlled to continue to hold the cup in the planned pose for the duration of cement curing (e.g., ten minutes). FIG. 16 illustrates step 322 in an example embodiment, and shows the implant cup 1600 held in position relative to the implant augment 1300 by a holder arm 1400. The holder arm 1400 may be the same device as the impaction device 1500 or a different device. By automating this holding task, a surgeon or surgical assistant may advantageously become free to accomplish other tasks relating to the surgical procedure. Additionally, robotically-assisted and tracked positioning during cement curing may ensure that the planned geometric relationship between the cup and the augment is achieved. Furthermore, integrity of the cement mantle and unitization of the cup and augment may be optimized because relative movement is minimized as the cement hardens.

Following step 322, the surgical procedure may proceed following established workflows, for example to position a liner in the cup, to position a femoral implant in the cup, to repair soft tissue proximate the hip joint, and to close the surgical incision. The surgical system 200 may be configured to assist with some or all of these additional steps in various embodiments. Process 300 may thereby improve surgical efficiency and experience for surgeons, reduce the duration of a surgical procedure, and improve patient outcomes by providing accurate placement of augments and cups in accordance with personalized surgical plans.

Although FIGS. 3-16 show embodiments relating to hip arthroplasty procedures, it should be understood that the systems and methods described with reference thereto may be adapted for shoulder arthroplasty procedures. For example, an augment, mesh, bone graft, or other supporting structure may be planned and installed at a glenoid following the workflow of process 300. In some embodiments, the augment may be customized for a particular patient (e.g., using additive manufacturing).

Figure 17:
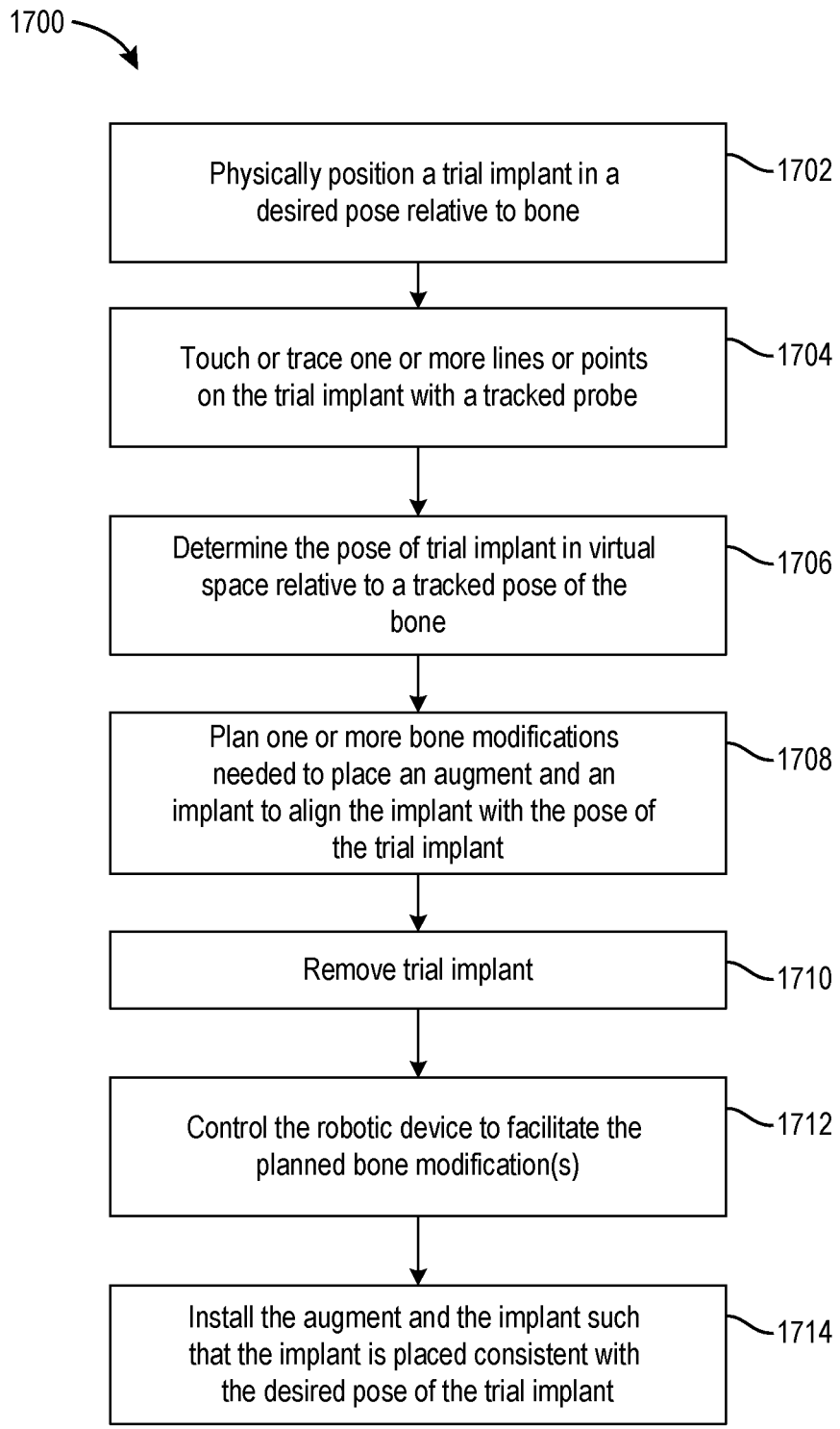
FIG. 17 is a flowchart of a process for facilitating a knee arthroplasty procedure that includes a tibial or femoral augment, according to an exemplary embodiment.

Referring now to FIG. 17, a flowchart of a process 1700 for facilitating the use of augments in knee arthroplasty procedures is shown, according to an exemplary embodiment. Process 1700 can be executed by the surgical system of FIG. 2 in some embodiments. In a total knee arthroplasty procedure, a tibia is prepared to be coupled to a tibial implant and a femur is prepared to be coupled to a femoral implant. Following the procedure, the tibial implant and the femoral implant will articulate on one another to provide knee function. One goal of a total knee arthroplasty procedure is to place the tibial and femoral implants in relative positions that ensure a full range of motion of the knee without pain or discomfort to the user. Another goal of a total knee arthroplasty procedure is to ensure that the tibial and femoral components are coupled to the tibia and femur is such a way as to withstand loads from functional use of the knee (e.g., standing, walking, running, biking, etc.). Accordingly, in some cases (e.g., bone decay, revision knee procedures, etc.) it may be desirable to use one or more augment components in addition to the tibial or femoral implants to provide structural support for the implants and facilitate placement of the implants in the preferred poses to improve patient outcomes.

At step 1702 of process 1700, a trial implant or template is physically positioned in a desired pose relative to a bone (e.g., a femur or tibia). In some cases, one or more cuts or other modifications may have been made to the bone during the knee arthroplasty procedure before step 1702. At step 1702, various tests may be perform to determine whether the trial implant is in a desired (proper, clinically-advantageous, etc.) pose. For example, a ligament balancing test may be performed.

When the trial implant has been positioned in the desired pose, at step 1704 a pose of a tracked probe is tracked while the probe is used to touch or trace one or more lines or points on the trial implant. The position and orientation of the tracked probe relative to a tracked position and orientation of the bone can be determined by a registration process as described above with reference to FIG. 2. FIGS. 18-21 illustrate example, non-limiting embodiments of step 1704.

Figure 18:
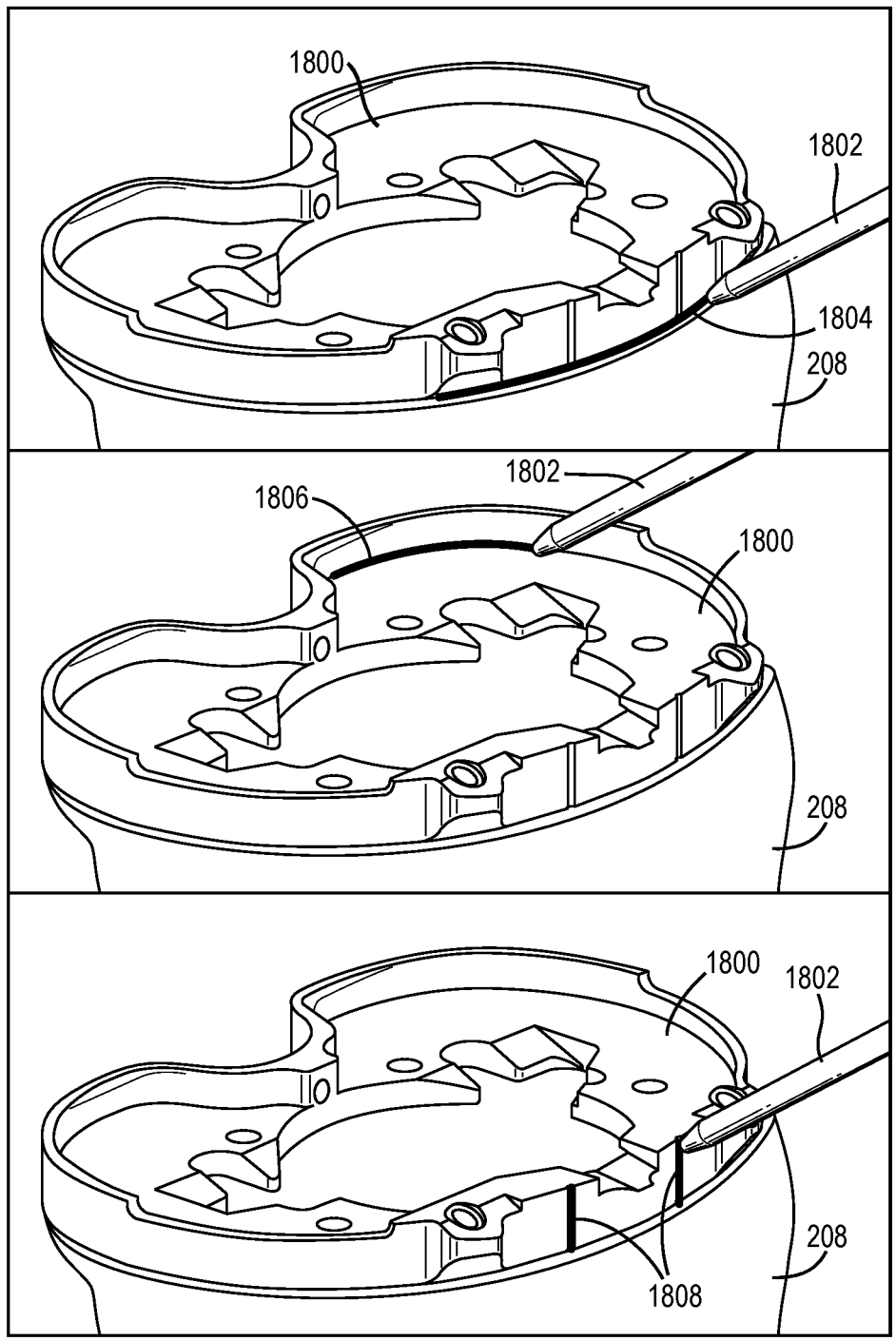
FIG. 18 is a first illustration of a tibial template and a probe as used in the process of FIG. 17, according to an exemplary embodiment.
Figure 19:
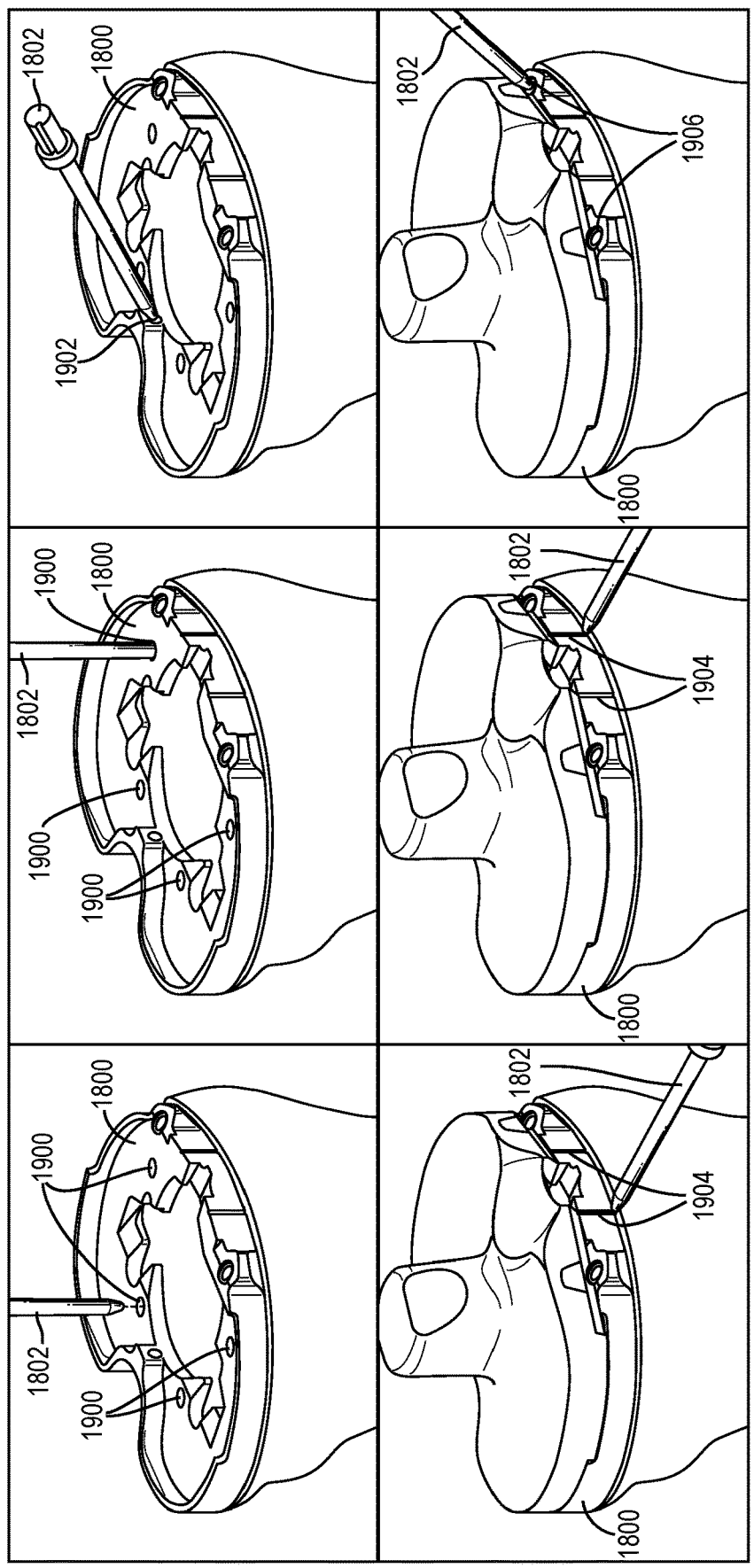
FIG. 19 is a second illustration of a tibial template and a probe as used in the process of FIG. 17, according to an exemplary embodiment.

As shown in FIGS. 18 and 19, a tibial template 1800 is positioned on a tibia 208. As shown in FIG. 18, A probe 1802 is traced along an anterior curve 1804 of the tibial template 1800, an inner profile 1806 of the tibial template 1800, and anterior ridges 1808 of the tibial template 1800. As shown in FIG. 19, a probe is touched to various points on the tibial template 1800, including headed nail holes 1900, tibial alignment handle dimple 1902, anterior reference marks 1904, and anterior nail holes 1906. Any combination of lines and points as shown in FIGS. 18-19 can be used at step 1704 for collecting points or lines at the tibial template 1800, or on another instrument or instruments fixed in position relative to the tibial template 1800.

Figure 20:
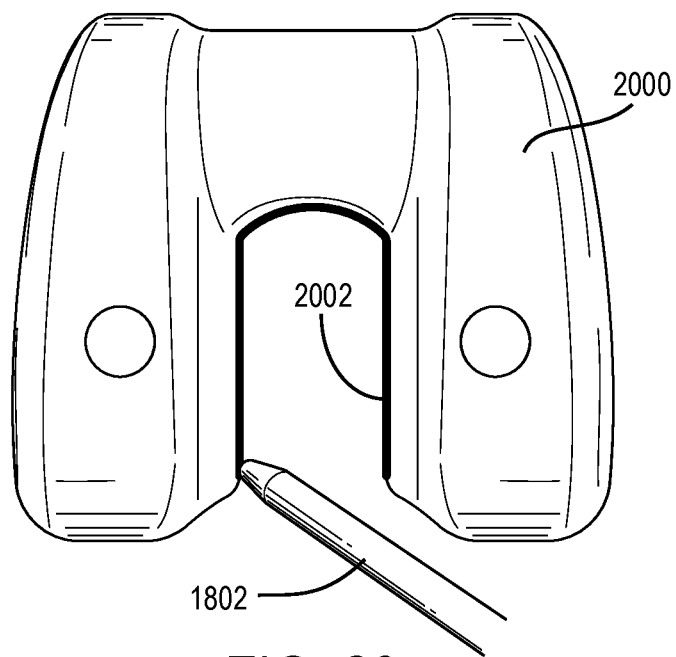
FIG. 20 is a first illustration of a femoral trial and a probe as used in the process of FIG. 17, according to an exemplary embodiment.
Figure 21:
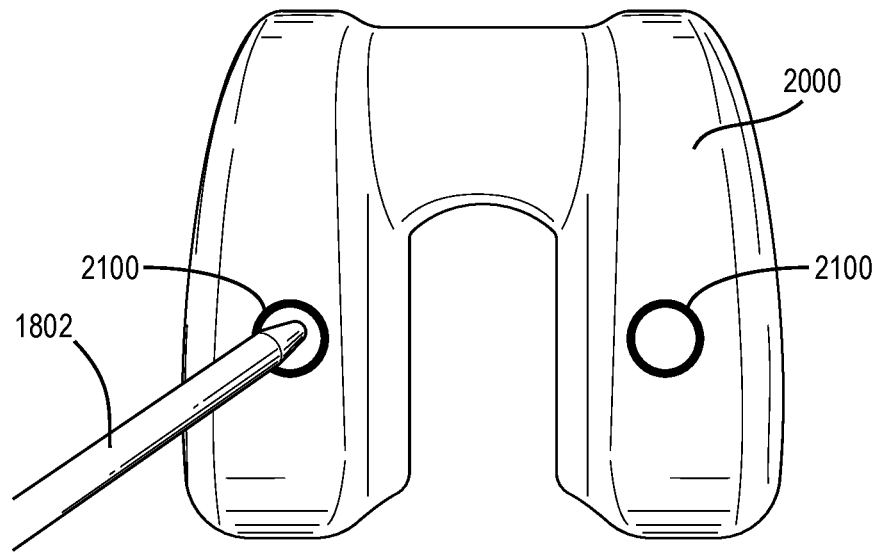
FIG. 21 is a second illustration of a femoral trial and a probe as used in the process of FIG. 17, according to an exemplary embodiment.

As shown in FIGS. 20-21, a femoral trial 2000 is used. FIG. 20 shows the probe 1802 used to trace the intercondylar notch 2002 of the femoral trail 2000. FIG. 21 shows the probe 1802 used to touch peg holes 2100. Any combination of lines and points as shown in FIGS. 20-21 can be used at step 1704 for collecting points or lines on the femoral trial 2000.

At step 1706, the pose of the trial implant in virtual space relative to a tracked pose of the bone (e.g., represented by a virtual model of the bone) is determined. For example, based on the tracked position of the probe 1802 when the various lines or points are touched at step 1704, a model of the trial implant can be oriented and positioned in virtual space relative to the virtual model of the bone. Accordingly, the points and lines used at step 1704 (and shown in FIGS. 18-21) are selected to provide sufficient data for accurate determination of the pose of the trial implant at step 1706.

In the example described herein, the pose of the trial implant is used as the planned pose for the implant (i.e., implant to be left in the patient after the procedure). In other examples, an offset or other adjustment may be made between the pose of the trial implant and the planned pose of the implant.

At step 1708, one or more bone modifications are planned (e.g., automatically by the processing circuit 260). The planned bone modification(s) prepares the bone to be coupled to an augment and to receive the augment and the implant such that the implant is positioned in the planned pose (e.g., the pose of the trial implant determined at step 1706). For example, an augment may be used to correct for bone loss or weakness on a first side of a bone. The augment may be selected automatically by the processing circuit 260 (e.g., from a set of possible augments of various sizes, types, shapes, etc.) based the pose of the trial implant and, in some cases, other pre- or intra-operative data. In such a case, a bone modification may be planned to remove a corresponding section of bone to allow for an augment to be securely placed to reinforce the connection between the implant and the bone. Various other updates, additions, etc. to the surgical plan may also be made at step 1708.

To facilitate explanation of step 1708, FIGS. 22-23 illustrate implants for knee arthroplasty procedures with augments. FIG. 22 shows a tibial implant 2200 and a tibial augment 2202. If the tibial augment 2202 is desired, at step 1708 a cut is planned to remove bone from the tibia to create space for the tibial augment 2202 to be received by the tibia 208. FIG. 23 shows a femoral implant 2204 with a pair of femoral augments 2206. If the femoral augments 2206 of FIG. 23 are desired, a pair of planar cuts are planned at step 1708 to remove bone from the femur to provide space for the pair of femoral implants 2204. Other types of cuts and resulting shapes (e.g., a volume reamed with a burr) may be used in other embodiments in accordance with the surface contours of the corresponding implant(s) and augment(s) used in a given procedure. For example, for different types of augments (e.g., cone augments, stems, etc.) corresponding resection shapes can be executed at step 1708.

At step 1710, the trial implant is removed from the surgical field. At step 1712, the robotic device 220 is controlled to facilitate the planned bone modifications. For example, the robotic device 220 may provide haptic feedback to facilitate a surgeon in executed the planned bone modifications using a surgical tool coupled to the robotic device 220 as described with reference to FIG. 2. As another example, the robotic device 220 may be controlled to autonomously execute the planned bone modification.

At step 1714, the augment and the implant are installed such that the implant is placed consistent with the desired pose of the trial implant ascertained at steps 1704-1706. In some embodiments, the augment and the implant are manually placed and the positions are checked using a tracked probe as for the trial implant at step 1704. In some embodiments, the robotic device 220 is controlled to hold the augment and/or implant in the planned pose and/or control a drill or other tool to facilitate and/or automate coupling of the augment and/or implant to the patient's bone (femur or tibia in the case of knee arthroplasty).

Process 1700 thereby provides for a robotically-assisted knee arthroplasty procedure that includes intraoperative planning and placement of an augment for either the tibial implant or the femoral implant. It should be understood that process 1700 and various other systems and methods described herein may be adapted for various indications, various surgical procedures, various anatomical regions, etc.

In some embodiments, data is collected relating to the planning and procedures conducted using the systems and methods described herein. For example, details such as the types of implants used, bone density, ligament balancing measurements, final implant placement (angle, anterior/posterior placement, medial/lateral placement, placement with respect to a joint line, mechanical and anatomic axis positions, etc.), among other possibilities, can be collected during planning of the procedures. Post-operative outcomes may also be collected. The post-operative outcomes may then be compared to the other data to provide insights into improved execution and implementation of the systems and methods described herein.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and are considered to be within the scope of the disclosure.

What is claimed is:

1. A method, comprising:
   obtaining a surgical plan comprising a first planned position of an implant and a second planned position of an augment relative to a bone, wherein the augment is planned to provide support between the bone and the implant;
   preparing the bone to receive both the implant in the first planned position and the augment in the second planned position by controlling a robotic device based on the first planned position of the implant and the second planned position of the augment;
   determining whether the augment is in the second planned position by tracking a probe as the probe is touched to the augment; and
   fixing the augment to the bone in response to determining that the augment is in the second planned position.

2. The method of claim 1, wherein controlling the robotic device comprises causing the robotic device to move in accordance with a virtual control object comprising a unified surface corresponding to both the implant and the augment.

3. The method of claim 1, wherein controlling the robotic device comprises causing the robotic device to separately move in accordance with (i) a first virtual control object corresponding to the implant and (ii) a second virtual control object corresponding to the augment.

4. The method of claim 3, wherein preparing the bone by controlling the robotic device comprises using the first virtual control object before using the second virtual control object.

5. The method of claim 1, wherein the augment is a cone.

6. The method of claim 1, wherein the augment is a stem.

7. The method of claim 1, wherein the augment is a spacer.

8. The method of claim 1, further comprising holding, by the robotic device, the augment at the bone in the second planned position to facilitate fixation of the augment to the bone.

9. The method of claim 1, further comprising preparing the bone to receive an additional augment planned to provide additional support for the implant.

10. One or more non-transitory computer-readable media storing instructions that, when executed by a processor, cause the processor to perform operations comprising:
obtaining a surgical plan comprising a first planned position of an implant and a second planned position of an augment relative to a bone, wherein the augment is positionable independent of the implant and is planned to provide support between the bone and the implant, wherein obtaining the surgical plan comprises allowing adjustment of the second planned position relative to the first planned position; and
assisting preparation of the bone to receive both the implant in the first planned position and the augment in the second planned position by controlling a robotic device based on the first planned position of the implant and the second planned position of the augment.

11. The one or more non-transitory computer-readable media of claim 10, wherein controlling the robotic device is based on a control object comprising a unified surface corresponding both the implant and the augment.

12. The one or more non-transitory computer-readable media of claim 10, wherein controlling the robotic device is based on a first control object corresponding to the implant and a second control object corresponding to the augment.

13. The one or more non-transitory computer-readable media of claim 12, wherein the operations comprise using the second control object in controlling the robotic device before using the first control object in controlling the robotic device.

14. The one or more non-transitory computer-readable media of claim 10, wherein the augment is a cone, a stem, or a spacer.

15. The one or more non-transitory computer-readable media of claim 10, wherein the operations further comprise controlling the robotic device to hold the augment at the bone in the second planned position.

16. The one or more non-transitory computer-readable media of claim 10, wherein the operations further comprise determining whether the augment is in the second planned position based on tracking data indicative of positions of a probe relative to the bone.

17. A system comprising:
a robotic device; and
circuitry programmed to:
obtain a surgical plan comprising a first planned position of an implant and a second planned position of an augment relative to a bone, wherein the augment is planned to at least partially fill a space between the bone and the implant, and wherein the second planned position is adjustable relative to the first planned position; and
assist preparation of the bone to receive both the implant in the first planned position and the augment in the second planned position by controlling the robotic device based on the first planned position of the implant and the second planned position of the augment.

18. The system of claim 17, further comprising the augment, wherein the augment is a cone.

19. The system of claim 17, further comprising the augment, wherein the augment is a stem.

20. The system of claim 17, further comprising the augment, wherein the augment is a spacer.

21. The system of claim 17, wherein the circuitry is further programmed to control the robotic device to hold the augment at the bone in the second planned position to assist fixation of the augment to the bone.

22. The system of claim 17, further comprising a probe and a tracking system configured to track the probe, wherein the circuitry is further programed to determine whether the augment is in the second planned position based on tracking of the probe by the tracking system as the probe is touched to the augment.

* * * * *